United States Patent
Park et al.

(10) Patent No.: US 9,534,210 B2
(45) Date of Patent: Jan. 3, 2017

(54) REVERSE TRANSCRIPTASE HAVING IMPROVED THERMOSTABILITY

(75) Inventors: Han Oh Park, Daejeon (KR); Sung Jun Yang, Daejeon (KR); Sung Mo Joo, Daejeon (KR); Byoung Oh Hwang, Pyeongtaek-si (KR)

(73) Assignee: BIONEER CORPORATION, Daejeon (KR)

( * ) Notice: Subject to any disclaimer, the term of this patent is extended or adjusted under 35 U.S.C. 154(b) by 0 days.

(21) Appl. No.: 13/984,746

(22) PCT Filed: Feb. 7, 2012

(86) PCT No.: PCT/KR2012/000894
§ 371 (c)(1),
(2), (4) Date: Oct. 18, 2013

(87) PCT Pub. No.: WO2012/108672
PCT Pub. Date: Aug. 16, 2012

(65) Prior Publication Data
US 2014/0045244 A1    Feb. 13, 2014

(30) Foreign Application Priority Data
Feb. 9, 2011    (KR) ........................ 10-2011-0011639

(51) Int. Cl.
*C12N 9/12*    (2006.01)
*C12N 1/20*    (2006.01)
(Continued)

(52) U.S. Cl.
CPC ............... *C12N 9/1276* (2013.01); *C12N 1/20* (2013.01); *C12N 9/12* (2013.01); *C12N 15/70* (2013.01); *C12P 19/34* (2013.01); *Y02P 20/52* (2015.11)

(58) Field of Classification Search
None
See application file for complete search history.

(56) References Cited

U.S. PATENT DOCUMENTS 4,554,101 A    11/1985  Hopp
6,140,086 A    10/2000  Fox et al.
(Continued)

FOREIGN PATENT DOCUMENTS

CN    101636505 A    1/2010
EP        1132470 B1    9/2005
(Continued)

OTHER PUBLICATIONS

Yasukawa et al., "Increase in thermal stability of Moloney murine leukaemia virus reverse transcriptase by site-directed mutagenesis", Journal of Biotechnology, vol. 150, pp. 299-306, 2010.*
(Continued)

*Primary Examiner* — Robert Mondesi
*Assistant Examiner* — Richard Ekstrom
(74) *Attorney, Agent, or Firm* — Rothwell, Figg, Ernst & Manbeck, P.C.

(57) ABSTRACT

The present invention relates to a reverse transcriptase having improved thermostability, more precisely a mutant reverse transcriptase with improved thermostability by substitution of one or more amino acids selected from the group consisting of the $63^{rd}$ glutamine (Q63), the $264^{th}$ lysine (K264), the $295^{th}$ lysine (K295), the $306^{th}$ threonine (T306), the $346^{th}$ glutamic acid (E346), the $408^{th}$ proline (P408), the $438^{th}$ histidine (H438), and the $454^{th}$ asparagin (N454) of the amino acid sequence of M-MLV originated reverse transcriptase represented by SEQ. ID. NO: 1 with other amino acids. The mutant reverse transcriptase of the present invention demonstrates excellent thermostability, compared with the wild type reverse transcriptase. Therefore, it is advan-
(Continued)

tageous to obtain the target cDNA with stable reverse transcription activity even in the presence of RNA that can form the stable secondary structure at a high temperature.

9 Claims, 11 Drawing Sheets

(51) Int. Cl.
*C12N 15/70* (2006.01)
*C12P 19/34* (2006.01)

(56) References Cited

U.S. PATENT DOCUMENTS

| | | |
|---|---|---|
| 6,485,917 B1 | 11/2002 | Yamamoto et al. |
| 6,518,019 B2 | 2/2003 | Gerard et al. |
| 7,056,716 B2* | 6/2006 | Potter et al. ............... 435/194 |
| 7,078,208 B2 | 7/2006 | Smith et al. |
| 2002/0090618 A1 | 7/2002 | Smith et al. |
| 2002/0119465 A1 | 8/2002 | Zhao et al. |
| 2003/0003452 A1 | 1/2003 | Potter et al. |
| 2003/0077762 A1 | 4/2003 | Yamamoto et al. |
| 2003/0198944 A1 | 10/2003 | Gerard et al. |
| 2004/0209276 A1* | 10/2004 | Smith et al. ............... 435/6 |
| 2007/0202529 A1 | 8/2007 | Gruber et al. |
| 2008/0227661 A1 | 9/2008 | Hogrefe et al. |
| 2009/0011408 A1 | 1/2009 | Sorge |
| 2011/0081704 A1* | 4/2011 | Smith et al. ............... 435/194 |
| 2011/0124050 A1 | 5/2011 | Engel et al. |
| 2012/0003645 A1* | 1/2012 | Yim et al. ............... 435/6.11 |
| 2012/0009630 A1* | 1/2012 | Lambowitz et al. ...... 435/91.51 |

FOREIGN PATENT DOCUMENTS

| | | |
|---|---|---|
| JP | 2009-504162 A | 2/2009 |
| WO | 01/92500 A1 | 12/2001 |
| WO | 2005/105142 A2 | 11/2005 |
| WO | 2007/022045 A2 | 2/2007 |
| WO | 2009/125006 A2 | 10/2009 |

OTHER PUBLICATIONS

B. Arezi et al.: "Novel mutations in Moloney Murine Leukemia Virus reverse transcriptase increase thermostability through tighter binding to template-primer," Nucleic Acids Research, 2009, vol. 37, No. 2, pp. 473-481.

I. Shevelev et al.: "The 3'-5' Exonucleases," Nature Rev. Mol. Cell Biol., vol. 3, 2002, pp. 1-12.

F. Perrino et al.: "Proofreading by the ε submit of *Escherichia coli* DNA polymerase III increases the fidelity of calf thymus DNA polymerase α," Proc. Natl. Acad. Sci. USA, vol. 86, 1989, pp. 3085-3088.

M. Bakhanashvili: "Exonucleolytic proofreading by p53 protein," Eur. J. Biochem., vol. 268, 2001, pp. 2047-2054.

P. Huang: "Excision of mismatched nucleotides from DNA: a potential mechanism for enhancing DNA replication fidelity by wild-type p53 protein," Oncogene, vol. 17, 1998, pp. 261-270.

J. Kyte et al.: "A Simple Method for Displaying the Hydropathic Character of a Protein," J. Mol. Biol., vol. 157, 1982, pp. 105-132.

P. Chou et al.: "Prediction of β-Turns," Biophys. J., vol. 26, 1979, pp. 367-384.

P. Chou et al.: "Prediction of Protein Conformation," Biochemistry, vol. 13, No. 2, 1974, pp. 222-245.

European Search Report cited in Application No. 15156411.9, dated Apr. 29, 2015, 7 pages.

* cited by examiner

Fig. 1

```
  1 mlniedehrl hetskepdvs lgstwlsdfp qawaetggmg lavrqaplii plkatstpvs 61 ikgypmsqea rlgikphiqr lldqgilvpc qspwntpllp vkkpgtndyr pvqdlrevnk
    →L
121 rvedihptvp npynllsglp pshqwytvld lkdaffclrl hptsqplfaf ewrdpemgis 181 gqltwtrlpq gfknsptlfd ealhrdladf riqhpdlill qyvddlllaa tseldcqqgt 241 rallqtlgnl gyrasakkaq icqkqvkylg yllkegqrwl tearketvmg qptpktprql
                         →L                                    →Q
301 reflgtagfc rlwipgfaem aaplypltkt gtlfnwgpdq qkayqikqa lltapalglp
    →L                                            →M
361 dltkpfelfv dekqgyakgv ltqklgpwrr pvaylskkld pvaagwppcl rmvaaiavlt
                                                            →E
421 kdagkltmgq plvilaphav ealvkqppdr wlsnarmthy qallldtdrv qfgpvvalnp
            →Y                →F
481 atllplpeeg lqhncldila eahgtrpdlt dqplpdadht wytdgssllq egqrkagaav 541 ttetevimak alpagtsaqr aelialtqal kmaegkklnv ytdsryafat ahihgeiyrr 601 rglltsegke iknkdeilal lkalflpkrl siihcpghqk ghsaeargnr madqaarkaa 661 itetpdtstl li
```

Fig. 2 mat_peptide 2337..4349

- gene="gag-pol"
- product="p80 RT"
- protein_id="NP_955591.1"
- db_xref="GI:40796138"

```
4    ctaaatatagaagatgagcatcggctacatgagacctcaaaagagccagatgtttctcta   63
     ||||||||||||||||||||||||||||||||||||||||||||||||||||||||||||
1    ctaaatatagaagatgagcatcggctacatgagacctcaaaagagccagatgtttctcta   60

64   gggtccacatggctgtctgattttcctcaggcctgggcggaaaccggggggcatgggactg  123
     ||||||||||||||||||||||||||||||||||||||||||||||||||||||||||||
61   gggtccacatggctgtctgattttcctcaggcctgggcggaaaccggggggcatgggactg  120

124  gcagttcgccaagctcctctgatcatacctctgaaagcaacctctaccccgtgtccata   183
     ||||||||||||||||||||||||||||||||||||||||||||||||||||||||||||
121  gcagttcgccaagctcctctgatcatacctctgaaagcaacctctaccccgtgtccata   180
```

Fig. 3

```
184  aaacaataccccatgtcacaagaagccagactggggatcaagccccacatacagagactg  243
     ||||||   ||||||||||||||||||||||||||||||||||||||||||||||||||||
181  aaactttaccccatgtcacaagaagccagactggggatcaagccccacatacagagactg  240
        Q63L: CAA→CTT 244  ttggaccagggaatactggtaccctgccagtcccctggaacacgccctgctacccgtt  303
     ||||||||||||||||||||||||||||||||||||||||||||||||||||||||||||
241  ttggaccagggaatactggtaccctgccagtcccctggaacacgccctgctacccgtt  300

304  aagaaaccagggactaatgattataggcctgtccaggatctgagagaagtcaacaagcgg  363
     ||||||||||||||||||||||||||||||||||||||||||||||||||||||||||||
301  aagaaaccagggactaatgattataggcctgtccaggatctgagagaagtcaacaagcgg  360

364  gtggaagacatccaccccaccgtgcccaaccttacaacctcttgagcgggctcccaccg  423
     ||||||||||||||||||||||||||||||||||||||||||||||||||||||||||||
361  gtggaagacatccaccccaccgtgcccaaccttacaacctcttgagcgggctcccaccg  420
```

Fig. 4

```
424  tcccaccagtggtacactgtgcttgatttaaaggatgccttttctgcctgagactccac  483
     ||||||||||||||||||||||||||||||||||||||||||||||||||||||||||
421  tcccaccagtggtacactgtgcttgatttaaaggatgccttttctgcctgagactccac  480

484  cccaccagtcagcctctcttcgcctttgagtggagagatccagagatgggaatctcagga  543
     ||||||||||||||||||||||||||||||||||||||||||||||||||||||||||
481  cccaccagtcagcctctcttcgcctttgagtggagagatccagagatgggaatctcagga  540

544  caattgacctggaccagactcccacagggtttcaaaaacagtcccaccctgtttgatgag  603
     ||||||||||||||||||||||||||||||||||||||||||||||||||||||||||
541  caattgacctggaccagactcccacagggtttcaaaaacagtcccaccctgtttgatgag  600

604  gcactgcacagagacctagcagacttccggatccagcacccagacttgatcctgctacag  663
     ||||||||||||||||||||||||||||||||||||||||||||||||||||||||||
601  gcactgcacagagacctagcagacttccggatccagcacccagacttgatcctgctacag  660

664  tacgtggatgacttactgctggccgccacttctgagctagactgccaacaaggtactcgg  723
     ||||||||||||||||||||||||||||||||||||||||||||||||||||||||||
661  tacgtggatgacttactgctggccgccacttctgagctagactgccaacaaggtactcgg  720
```

Fig. 5

```
724  gccctgttacaaaccctagggaacctcgggtatcgggcctcggccaagaaagcccaaatt 783
     ||||||||||||||||||||||||||||||||||||||||||||||||||||||||||||
721  gccctgttacaaaccctagggaacctcgggtatcgggcctcggccaagaaagcccaaatt 780

784  tgccagaaacaggtcaagtatctggggtatcttctaaaagagggtcagagatggctgact 843
     ||||||||||||||||||||||||||||||||||||||||||||||||||||||||||||
781  tgccagcttcaggtcaagtatctggggtatcttctaaaagagggtcagagatggctgact 840
         K264L: AAA→CTT 844  gaggccagaaaagagactgtgatggggcagcctactccgaagacccctcgacaactaagg 903
     ||||||||||||||||||||||||||||||||||||||||||||||||||||||||||||
841  gaggccagaaaagagactgtgatggggcagcctactccgcaaaccctcgacaactaagg 900
                                             K295Q: AAG→CAA 904  gagttcctagggacggcaggcttctgtcgcctctggatccctgggtttgcagaaatggca 963
     ||||||||||||||||||||||||||||||||||||||||||||||||||||||||||||
901  gagttcctagggCTTgcaggcttctgtcgcctctggatccctgggtttgcagaaatggca 960
                T306L: ACG→CTT
```

Fig. 6

```
 964 gcccccttgtaccctctcaccaaaacggggactctgtttaattggggcccagaccaacaa 1023
     ||||||||||||||||||||||||||||||||||||||||||||||||||||||||||||
 961 gcccccttgtaccctctcaccaaaacggggactctgtttaattggggcccagaccaacaa 1020

1024 aaggcctatcaagaaatcaagcaagctcttctaactgcccagccctggggttgccagat 1083
     ||||||||||||||||||||||||||||||||||||||||||||||||||||||||||||
1021 aaggcctatcaaatgatcaagcaagctcttctaactgcccagccctggggttgccagat 1080
             E346M: GAA→ATG 1084 ttgactaagccctttgaactctttgtcgacgagaagcaggctacgccaaggtgtccta 1143
     ||||||||||||||||||||||||||||||||||||||||||||||||||||||||||||
1081 ttgactaagccctttgaactctttgtcgacgagaagcaggctacgccaaggtgtccta 1140

1144 acgcaaaaactgggaccttggcgtcggccggtggcctacctgtccaaaaagctagaccca 1203
     ||||||||||||||||||||||||||||||||||||||||||||||||||||||||||||
1141 acgcaaaaactgggaccttggcgtcggccggtggcctacctgtccaaaaagctagaccca 1200

1204 gtagcagctgggtggccccttgcctacggatggtagcagccattgccgtactgacaaag 1263
     ||||||||||||||||||||||||||||||||||||||||||||||||||||||||||||
1201 gtagcagctgggtggcccgaatgcctacggatggtagcagccattgccgtactgacaaag 1260
                  P408E: CCT→GAA
```

Fig. 7

```
1264 gatgcaggcaagctaaccatgggacagccactagtcattctggcccccatgcagtagag 1323
     ||||||||||||||||||||||||||||||||||||||||||||||||||||||||||
1261 gatgcaggcaagctaaccatgggacagccactagtcattctggccccctacgcagtagag 1320
                                                     H438Y: CAT→TAC 1324 gcactagtcaaacaaccccccgaccgctggctttccaacgcccggatgactcactatcag 1383
     ||||||||||||||||||||||||||||||||||||||||||||||||||||||||||
1321 gcactagtcaaacaaccccccgaccgctggctttccttcgcccggatgactcactatcag 1380
                                         N454F: AAC→TTC 1384 gccttgcttttggacacggaccgggtccagttcggaccggtggtagccctgaacccggct 1443
     ||||||||||||||||||||||||||||||||||||||||||||||||||||||||||
1381 gccttgcttttggacacggaccgggtccagttcggaccggtggtagccctgaacccggct 1440

1444 acgctgctcccactgcctgaggaagggctgcaacacaactgccttgatatcctggccgaa 1503
     ||||||||||||||||||||||||||||||||||||||||||||||||||||||||||
1441 acgctgctcccactgcctgaggaagggctgcaacacaactgccttgatatcctggccgaa 1500
```

Fig. 8

```
1504 gcccacggaacccgacccgacctaacggaccagccgctcccagacgccgaccacacctgg 1563
     ||||||||||||||||||||||||||||||||||||||||||||||||||||||||||||
1501 gcccacggaacccgacccgacctaacggaccagccgctcccagacgccgaccacacctgg 1560

1564 tacacggatggaagcagtctcttacaagagggacagcgtaaggcgggagctgcggtgacc 1623
     ||||||||||||||||||||||||||||||||||||||||||||||||||||||||||||
1561 tacacggatggaagcagtctcttacaagagggacagcgtaaggcgggagctgcggtgacc 1620

1624 accgagaccgaggtaatctgggctaaagccctgccagccgggacatccgctcagcgggct 1683
     ||||||||||||||||||||||||||||||||||||||||||||||||||||||||||||
1621 accgagaccgaggtaatctgggctaaagccctgccagccgggacatccgctcagcgggct 1680

1684 gaactgatagcactcacccaggccctaaagatggcagaaggtaagaagctaaatgtttat 1743
     ||||||||||||||||||||||||||||||||||||||||||||||||||||||||||||
1681 gaactgatagcactcacccaggccctaaagatggcagaaggtaagaagctaaatgtttat 1740

1744 actgatagccgttatgcttttgctactgcccatatccatggagaaatatacagaaggcgt 1803
     ||||||||||||||||||||||||||||||||||||||||||||||||||||||||||||
1741 actgatagccgttatgcttttgctactgcccatatccatggagaaatatacagaaggcgt 1800
```

Fig. 9

```
1804 gggttgctcacatcagaaggcaaagagatcaaaaataaagacgagatcttggccctacta 1863
     ||||||||||||||||||||||||||||||||||||||||||||||||||||||||||||
1801 gggttgctcacatcagaaggcaaagagatcaaaaataaagacgagatcttggccctacta 1860

1864 aaagccctctttctgcccaaaagacttagcataatccattgtccaggacatcaaaaggga 1923
     ||||||||||||||||||||||||||||||||||||||||||||||||||||||||||||
1861 aaagccctctttctgcccaaaagacttagcataatccattgtccaggacatcaaaaggga 1920

1924 cacagcgccgaggctagaggcaaccggatggctgaccaagcggcccgaaaggcagccatc 1983
     ||||||||||||||||||||||||||||||||||||||||||||||||||||||||||||
1921 cacagcgccgaggctagaggcaaccggatggctgaccaagcggcccgaaaggcagccatc 1980

1984 acagagactccagacacctctaccctcctcata 2016
     |||||||||||||||||||||||||||||||||
1981 acagagactccagacacctctaccctcctcata 2013
```

REVERSE TRANSCRIPTASE HAVING IMPROVED THERMOSTABILITY

CROSS REFERENCE TO RELATED APPLICATIONS

This application is a 35 U.S.C. §371 National Phase Entry application from PCT/KR2012/000894, filed Feb. 7, 2012, and designating the United States, which claims priority under 35 U.S.C. §119 to Korean Patent Application No. 10-2011-0011639 filed Feb. 9, 2011, which is incorporated herein in its entirety.

The present application includes a Sequence Listing filed in electronic format. The Sequence Listing is entitled "3510-119_ST25.txt" created on Sep. 20, 2013, and is 109,000 bytes in size. The information in the electronic format of the Sequence Listing is part of the present application and is incorporated herein by reference in its entirety.

TECHNICAL FIELD

The present invention relates to a reverse transcriptase, more precisely a reverse transcriptase having improved thermostability by mutating a specific amino acid residue composing the conventional reverse transcriptase.

BACKGROUND ART

Many studies have been undergoing about RNA tumor virus, particularly Moloney-Murine Leukemia Virus (M-MLV), human HIV, or Avian Myeloblastosis Virus (AMV) originated reverse transcriptases and accordingly their functions and properties have been disclosed. Reverse transcriptase has been used for many molecular biological methods such as cDNA library construction, reverse transcription and polymerase chain reaction (PCR), etc, owing to its unique characteristics favoring the synthesis of complementary DNA (cDNA) by using RNA as a template.

Three prototypes of retrovirus reverse transcriptase have been mainly studied. Moloney-Murine Leukemia Virus originated reverse transcriptase contains 78 kDa single subunit having RNA dependent DNA polymerase and RNase H activity. The said enzyme is cloned and expressed in E. coli as an authentic active form. HIV originated reverse transcriptase is hetero-dimer of p66 and p51 subunits. P51 subunit is generated by proteolytic cleavage of p66 subunit. P66 subunit contains both RNA dependent DNA polymerase and RNase H domains, but p51 subunit contains only DNA polymerase domain. Active HIV originated p66/p51 reverse transcriptase is cloned and expressed in many expression hosts including E. coli. In HIV p66/p51 hetero-dimer, 51 kDa subunit is catalytically inactive and 66 kDa subunit shows both DNA polymerase activity and RNase H activity. In the meantime, Avian Sarcoma-Leukosis Virus (ASLV) reverse transcriptases such as Rous Sarcoma Virus (RSV) reverse transcriptase, Avian Myeloblastosis Virus reverse transcriptase, Avian Erythroblastosis Virus (AEV) helper virus MCAV reverse transcriptase, Avian Myelocytomatosis Virus MC29 helper virus MCAV reverse transcriptase, Avian Reticuloendotheliosis Virus (REV-T) helper virus REV-A reverse transcriptase, Avian Sarcoma Virus UR2 helper virus UR2AV reverse transcriptase, Avian Sarcoma Virus Y73 helper virus YAV reverse transcriptase, Rous Associated Virus (RAV) reverse transcriptase, and Myeloblastosis Associated Virus (MAV) reverse transcriptase are hetero-dimer of two subunits of alpha (approximately 62 kDa) and beta (approximately 94 kDa). Alpha subunit is generated by proteolytic cleavage of beta subunit. ASLV reverse transcriptase can exist in two catalytically active structures of alpha/beta and beta/beta. From the sediment analysis, it was confirmed that the said alpha/beta and beta/beta structures are dimmers and the alpha herein exists in the equilibrium state between monomer and dimer. ASLV alpha/beta or beta/beta reverse transcriptase is the only retrovirus reverse transcriptase informed up to date to have three different activities such as DNA polymerase activity, RNase H activity, and DNA endonuclease (integrase) activity. The alpha structure has neither integrase domain nor its activity.

The conversion of mRNA to cDNA by reverse transcriptase mediated reverse transcription is very important in the studies on gene expression. However, it is not preferred in many ways to use untransformed reverse transcriptase as a mediator for reverse transcription. Reverse transcriptase happens to degrade RNA template by RNase H activity before the first strand reaction begins or when it is completed. There is also a chance of error in the first strand of cDNA by mis-priming of mRNA template. In fact, during cDNA synthesis, HIV reverse transcriptase makes errors as many as 1 nucleotide error per 3,000-6,000 nucleotides, while AMV reverse transcriptase makes 1 nucleotide error per 10,000 nucleotides.

Another factor that affects the effect of reverse transcriptase is whether RNA can form the secondary structure or not. Such secondary structure can be formed when RNA molecular has enough complementarity to generate double-stranded RNA. In general, the formation of RNA secondary structure can be reduced by increasing the temperature of RNA molecule containing solution. So, it is preferred to perform reverse transcription of RNA at higher than 37° C. The reverse transcriptase of the present invention loses its activity when the culture is performed at much higher temperature than 37° C. (for example, at 50° C.)

A variety of methods to process thermostable reverse transcriptase are informed in the prior art, which include the method using thermostable DNA polymerase having reverse transcriptase activity, the method increasing reverse transcriptase activity by inducing mutation in thermostable DNA polymerase, the method inducing mutation in thermo-unstable reverse transcriptase, the method using $Mn^{2+}$ instead of $Mg^{2+}$ in the presence of Taq/Tth DNA polymerase, and the method using such additive as trehalose along with thermo-unstable reverse transcriptase.

To increase fidelity of polymerization of DNA or RNA template, those people skilled in the art have been using various enzyme compositions and methods. For example, Shevelev et al. provide a review article about 3'-5' exonuclease (Shevelev et al., *Nature Rev. Mol. Cell. Biol.* 3:364 (2002)). Perrino et al. use the upsilon subunit of *E. coli* DNA polymerase III to increase fidelity of calf thymus DNA polymerase alpha (Perrino et al., PNAS USA, 86:3085 (1989)). Bakhanashvili explains proofreading activity of p53 protein (Bakhanashvili, *Eur. J. Biochem.* 268:2047 (2001)), while Huang et al. describe the use of p53 to increase fidelity of DNA replication (Huang et al., *Oncogene*, 17:261 (1998)). US Patent Publication No. 2003/0198944A1 and U.S. Pat. No. 6,518,19 describe the enzyme mixture containing one or more reverse transcriptases (each reverse transcriptase has different transcription termination site) and if necessary containing one or more DNA polymerases additionally. US Patent Publication No. 2002/0119465A1 describes the composition containing mutant thermostable DNA polymerase and mutant reverse transcriptase (for example, mutant Taq DNA polymerase and mutant MMLV-RT). U.S. Pat. No. 6,485,917B1, US Patent Publication No.

2003/0077762, and European Patent Publication No. EP1132470 describe the method of cDNA synthesis in the presence of α-type DNA polymerase having 3'-5' exonuclease activity and the enzyme having reverse transcriptase activity.

When RNase H activity of reverse transcriptase is eliminated, the problem of RNA degradation of RNA template can be excluded, and further reverse transcription efficiency can be improved. However, such reverse transcriptase ('RNase H−' type) cannot solve the problems of mispriming and the generation of mRNA secondary structure. The conventional reverse transcriptase has low thermostability, and thus reverse transcription is only induced at comparatively low temperature. Accordingly, reverse transcription product cannot be efficiently obtained by the interruption of RNA secondary structure formed generally at as high temperature as at least 65° C. Such limitation is a major barrier not only for the synthesis of cDNA from the full-length RNA but also for various biochemical experiments requiring reverse transcription such as RNA detection and profiling. Therefore, it is highly required to develop a novel reverse transcriptase having stable reverse transcription activity even at high temperature.

DISCLOSURE

Technical Problem

The present invention is presented to solve the problem of the conventional reverse transcriptase as explained above. Therefore, it is an object of the present invention to provide a reverse transcriptase having improved thermostability that is effective in producing cDNA stably prepared by mutating a specific amino acid residue of M-MLV originated reverse transcriptase in order to give excellent reverse transcription activity even at higher temperature than the temperature allowing structural changes of RNA.

Technical Solution

Terms and techniques described in this invention indicate the general meaning understood by those in the art, unless stated otherwise. References described in this invention to explain the present invention are all included in this description.

In this invention, the term "reverse transcriptase activity" or "reverse transcription" indicates the capability of enzyme to synthesize DNA strand (that is, complementary DNA or cDNA) using RNA as a template. In this invention, "reverse transcriptase" is an enzyme that shows the reverse transcriptase activity when the enzyme activity is measured by the method described in this description or by any conventional method informed to those in the art.

In this invention, the term "reverse transcription activity" or "reverse transcriptase activity" is reciprocally used to indicate the capability of enzyme to synthesize DNA strand (that is, cDNA) using RNA as a template.

In this invention, the term "variation" or "mutation" indicates the change introduced in wild type DNA sequence to change amino acid sequence encoded by DNA. Herein, substitution, insertion, deletion, and point mutation, etc, are included, but not always limited thereto.

In this invention, the term "wild type" indicates the gene or gene product having the same properties as the gene or gene product separated from the natural source. On the contrary, the term "modified" or 'mutant' indicates the gene or gene product showing changed or different properties from the wild type gene or gene product.

In this invention, the term "expression vector" indicates the expression cassette in which one or more transcription regulatory regions necessarily including coding sequence and promoter are operatively linked or the vector containing the said expression cassette.

In this invention, the term "coding sequence" indicates the DNA sequence encoding specific amino acids or functional RNA.

In this invention, the term "promoter" indicates the region inducing transcription of coding sequence to RNA, particularly the region where polymerase and transcription factors are combined.

In this invention, the amino acid residues composing reverse transcriptase are presented as 3 or 1 alphabet abbreviation as shown in Table 1.

TABLE 1

| alanine | A | Ala |
|---|---|---|
| cysteine | C | Cys |
| aspartic acid | D | Asp |
| glutamic acid | E | Glu |
| phenylalanine | F | Phe |
| glycine | G | Gly |
| histidine | H | His |
| isoleucine | I | Ile |
| lysine | K | Lys |
| leucine | L | Leu |
| methionine | M | Met |
| asparagin | N | Asn |
| proline | P | Pro |
| glutamine | Q | Gln |
| arginine | R | Arg |
| serine | S | Ser |
| threonine | T | Thr |
| selenocysteine | U | Sec |
| valine | V | Val |
| tryptophan | W | Trp |
| tyrosine | Y | Tyr |

Hereinafter, the present invention is described in detail.

The present invention provides a reverse transcriptase having improved thermostability by substituting one or more amino acid residues selected from the group consisting of the $63^{rd}$ glutamine (Q63), the $264^{th}$ lysine (K264), the $295^{th}$ lysine (K295), the $306^{th}$ threonine (T306), the $346^{th}$ glutamic acid (E346), the $408^{th}$ proline (P408), the $438^{th}$ histidine (H438), and the $454^{th}$ asparagin (N454) of the amino acid sequence of M-MLV originated reverse transcriptase represented by SEQ. ID. NO: 1 with other amino acid residues.

The substitution of amino acid herein includes one or more substitutions selected from the group consisting of substitution of the $63^{rd}$ glutamine with leucine (Q63L), substitution of the $264^{th}$ lysine with leucine (K264L), substitution of the $295^{th}$ lysine with glutamine (K295Q), substitution of the $306^{th}$ threonine with leucine (T306L), substitution of the $346^{th}$ glutamic acid with methionine (E346M), substitution of the $408^{th}$ proline with glutamic acid (P408E), substitution of the $438^{th}$ histidine with tyrosine (H438Y), and substitution of the $454^{th}$ asparagin with phenylalanine (N454F), but not always limited thereto (see FIG. 1). In a preferred embodiment of the present invention, the thermostability of 8 mutant reverse transcriptases having the amino acid sequences each represented by SEQ. ID. NO: 2~NO: 9, in which the said 8 amino acid sites were substituted, was confirmed. Even if at least 2 amino acid sites were simultaneously mutated in the reverse transcriptase, it can be included in the spirit and scope of the present invention as long as it showed thermostability at high temperature.

In a preferred embodiment of the present invention, the mutant reverse transcriptases of the present invention demonstrated higher thermostability than the wild type reverse transcriptase. Among those mutants, K295Q, T306L, and P408E demonstrated excellent thermostability (see FIG. 10). In particular, the mutant reverse transcriptase T306L showing the highest thermostability demonstrated higher thermostability at the temperatures of 60° C., 65° C. and 70° C. with producing cDNA than the wild type M-MLV originated reverse transcriptase (see FIG. 11).

Those skilled in the art are well aware of that even when the amino acid substituted once is replaced again with another amino acid having similar characteristics (that is, conservative amino acid substitution), similar physiological and biochemical properties are still observed. The effect of amino acid substitution on the various amino acid properties and protein structure and functions has been targeted by those in the art.

For example, hydropathic index of amino acid can be considered (Kyte & Doolittle, 1982, *J. Mol. Biol.*, 157:105-132). Relative hydropathic property of amino acid is attributed to the secondary structure of the generated protein, which is used for the determination of interaction of other molecules. Each amino acid has hydropathic index based on its hydrophobicity and charge characteristics (Kyte & Doolittle, 1982, *J. Mol. Biol.*, 157:105-132), which is as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamic acid (−3.5); glutamine (−3.5); aspartic acid (−3.5); asparagin (−3.5); lysine (−3.9); and arginine (−4.5). In conservative substitution, it is preferred to use the amino acid having the hydropathic index of less than ±2, and the amino acid having the hydropathic index of less than ±1 is more preferred and the amino acid having the hydropathic index of less than ±0.5 is most preferred.

For the amino acid substitution, hydrophilicity of an amino acid residue can be also considered (see U.S. Pat. No. 4,554,101). Each amino acid residue has its own hydrophilicity value, which is as follows: arginine (+3.0); lysine (+3.0); aspartic acid (+3.0); glutamic acid (+3.0); serine (+0.3); asparagin (+0.2); glutamine (+0.2); glycine (0); threonine (−0.4); proline (−0.5+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). It is preferred to replace an amino acid residue with the one having similar hydrophilicity, but not always limited thereto.

The size of amino acid side chain can be also considered. For example, it is not preferred to replace such amino acid having densed side chain such as glycine or serine with the amino acid having big side chain such as tryptophan or tyrosine. The effect of various amino acid residues on the secondary structure of protein can be also considered. Through the experience obtained from the previous studies, it has been disclosed and measured that amino acid residues have effect on the selection of secondary structure of protein domain such as alpha-helix, beta-sheet, or reverse turn (Chou & Fasman, 1974, *Biochemistry*, 13:222-245; 1978, *Ann. Rev. Biochem.*, 47:251-276; 1979, *Biophys. J.*, 26:367-384).

Based on the broad experimental studies and the said considerations, the conservative amino acid substitution table has been made, which has been well informed to those in the art. Some examples are as follows: arginine and lysine; glutamic acid and aspartic acid; serine and threonine; glutamine and asparagin; and valine, leucine and isoleucine. Other examples are as follows: Ala(A) leu, ile, val; Arg(R) gln, asn, lys; Asn(N) his, asp, lys, arg, gln; Asp(D) asn, glu; Cys(C) ala, ser; Gln(O) glu, asn; Glu(E) gln, asp; Gly(G) ala; H is (H) asn, gln, lys, arg; Ile(I) val, met, ala, phe, leu; Leu(L) val, met, ala, phe, ile; Lys(K) gln, asn, arg; Met(M) phe, ile, leu; Phe(F) leu, val, ile, ala, tyr; Pro(P) ala; Ser(S), thr; Thr(T) ser; Trp(W) phe, tyr; Tyr(Y) trp, phe, thr, ser; Val(V) ile, leu, met, phe, ala.

For the amino acid substitution, it can be also considered whether the target residue is located in the inside of the protein or exposed to the solvent. If the residue is in the inside, conservative substitution includes as follows: Asp and Asn; Ser and Thr; Ser and Ala; Thr and Ala; Ala and Gly; Ile and Val; Val and Leu; Leu and Ile; Leu and Met; Phe and Tyr; and Tyr and Trp. If the residue is exposed on the solvent, conservative substitution includes as follows: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; and Phe and Tyr.

Before determining amino acid substitution, intramolecular or intermolecular conjugation such as disulfide bond between neighboring cysteine residues or ionic bond (salt bridge) between positive charged residue (for example, H is, Arg, and Lys) and negative charged residue (for example Asp, and Glu) is preferably considered.

The present invention also provides a gene encoding the said reverse transcriptase having improved thermostability.

The said gene is the gene encoding the mutant reverse transcriptase harboring one or more amino acid substations selected from the group consisting of substitution of the $63^{rd}$ glutamine of the wild type reverse transcriptase represented by SEQ. ID. NO: 1 with leucine (Q63L), substitution of the $264^{th}$ lysine of the wild type reverse transcriptase represented by SEQ. ID. NO: 1 with leucine (K264L), substitution of the $295^{th}$ lysine of the wild type reverse transcriptase represented by SEQ. ID. NO: 1 with glutamine (K295Q), substitution of the $306^{th}$ threonine of the wild type reverse transcriptase represented by SEQ. ID. NO: 1 with leucine (T306L), substitution of the $346^{th}$ glutamic acid of the wild type reverse transcriptase represented by SEQ. ID. NO: 1 with methionine (E346M), substitution of the $408^{th}$ proline of the wild type reverse transcriptase represented by SEQ. ID. NO: 1 with glutamic acid (P408E), substitution of the $438^{th}$ histidine of the wild type reverse transcriptase represented by SEQ. ID. NO: 1 with tyrosine (H438Y), and substitution of the $454^{th}$ asparagin of the wild type reverse transcriptase represented by SEQ. ID. NO: 1 with phenylalanine (N454F). In a preferred embodiment of the present invention, the gene of the invention is preferably the gene having one of the nucleotide sequences each represented by SEQ. ID. NO: 11~NO: 18 encoding 8 mutant reverse transcriptases having the amino acid sequences each represented by SEQ. ID. NO: 2~NO: 9 in which the said 8 amino acid sites are substituted. Any random gene encoding the mutant reverse transcriptase having at least two amino acid substitutions selected from the group consisting of the $63^{rd}$ glutamine (Q63), the $264^{th}$ lysine (K264), the $295^{th}$ lysine (K295), the $306^{th}$ threonine (T306), the $346^{th}$ glutamic acid (E346), the $408^{th}$ proline (P408), the $438^{th}$ histidine (H438), and the $454^{th}$ asparagin (N454) of the M-MLV originated reverse transcriptase represented by SEQ. ID. NO: 1 can be included in the spirit and scope of the present invention (see FIG. 2-FIG. 9).

In addition to the said genes hereinabove, polynucleotides which are actually identical or have same functions as the said genes can be included in the present invention. The phrase "actually identical or have same functions" herein indicates that two polynucleotides demonstrate at least 70% homology, preferably at least 80%, more preferably at least 90%, and most preferably at least 95% homology when they are properly arranged by well-informed computerized algorithm or investigation.

The present invention also provides an expression vector containing the said gene.

The mother vector used for the construction of the expression vector of the present invention is not limited, and any conventional vector for the transformation of prokaryotes or eukaryotes can be used. In a preferred embodiment of the present invention, recombinant expression vectors were constructed by inserting each mutant gene represented by SEQ. ID. NO: 11-NO: 18 into PET 22b(+), the extranuclear gene vector.

The present invention also provides a transformant transformed by the said expression vector.

The transformant of the present invention can be easily constructed by inserting the said expression vector into random prokaryotic cells or eukaryotic cells. The method to introduce a specific vector into cells is well-known to those in the art. Lipofectamine method is an example of the methods. In a preferred embodiment of the present invention, the PET 22b(+) vector introduced with the mutant gene was introduced in *E. coli* DH5α, leading to the construction of a transformant.

The present invention also provides a kit for reverse transcription comprising the said reverse transcriptase.

The kit for reverse transcription of the present invention can additionally include, in addition to the said reverse transcriptase, any conventional constituent necessary for reverse transcription such as a primer pair binding specifically to the target gene or oligonucleotide for amplification, dNTP, and reaction buffer, and DNA polymerase if necessary.

Advantageous Effect

The mutant reverse transcriptase of the present invention demonstrates excellent thermostability, compared with the wild type reverse transcriptase. Therefore, even in the presence of specific RNA that can form a very stable secondary structure at a high temperature which is a barrier for the efficient reverse transcription, the stable reverse transcription activity can be induced to give wanted cDNA with the reverse transcriptase of the present invention.

DESCRIPTION OF DRAWINGS

The application of the preferred embodiments of the present invention is best understood with reference to the accompanying drawings, wherein:

FIG. 1 is a diagram showing the sites and kinds of amino acids mutated in the mutant reverse transcriptase of the present invention.

FIG. 2-FIG. 9 are diagrams showing the sites and sequences of nucleotides mutated in the gene encoding the mutant reverse transcriptase of the present invention.

BEST MODE

Figure 10:
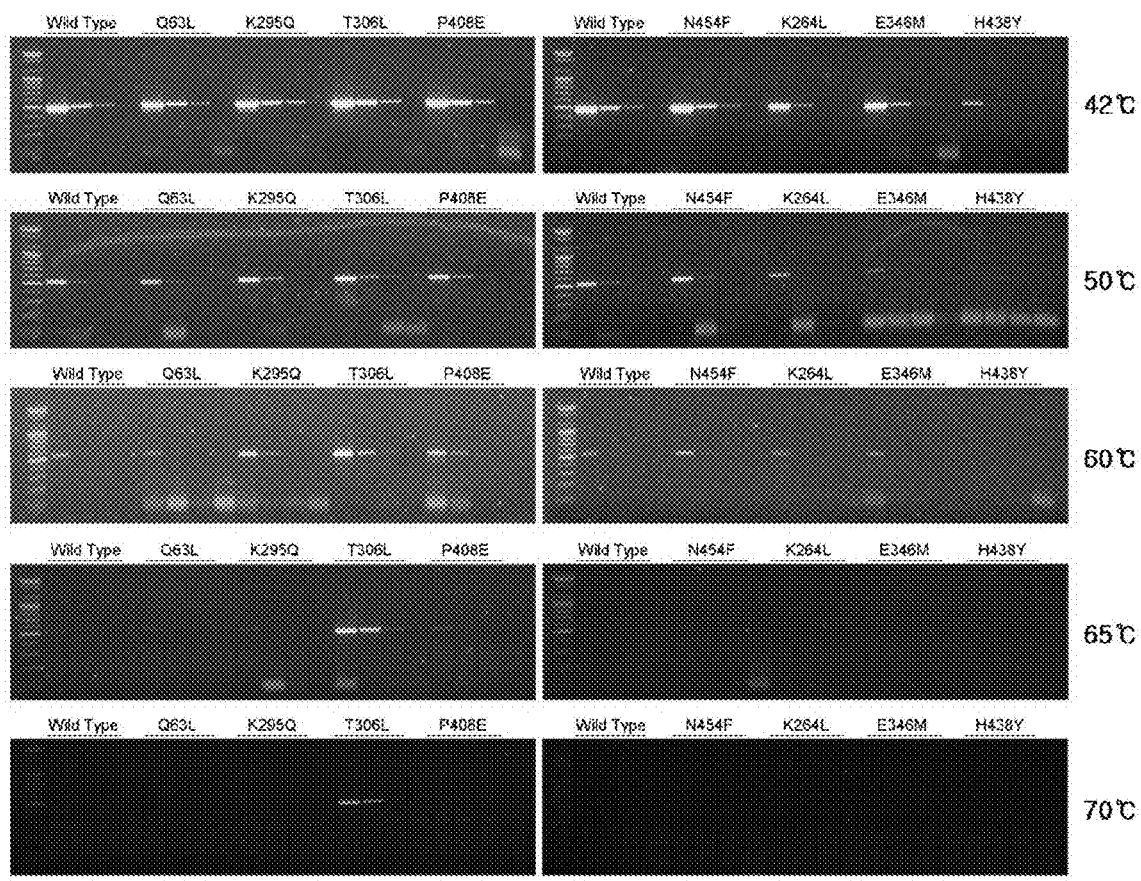
FIG. 10 is a set of electrophoresis photographs showing the results of reverse transcription induced by using the wild type reverse transcriptase (SEQ. ID. NO: 1) and the mutant reverse transcriptases of the present invention (SEQ. ID. NO: 2~NO: 9) at 42° C., at 50° C., at 60° C., at 65° C., and at 70° C.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Construction of Gene Encoding the Mutant Reverse Transcriptase

To induce mutation in the M-MLV originated reverse transcriptase having the amino acid sequence represented by SEQ. ID. NO: 1, nucleotide sequence of the gene encoding the M-MLV originated reverse transcriptase was substituted. Particularly, 8 mutant reverse transcriptases each harboring substitution of the 63$^{rd}$ glutamine of the M-MLV originated reverse transcriptase represented by SEQ. ID. NO: 1 with leucine (Q63L), substitution of the 264$^{th}$ lysine of the M-MLV originated reverse transcriptase represented by SEQ. ID. NO: 1 with leucine (K264L), substitution of the 295$^{th}$ lysine of the M-MLV originated reverse transcriptase represented by SEQ. ID. NO: 1 with glutamine (K295Q), substitution of the 306$^{th}$ threonine of the M-MLV originated reverse transcriptase represented by SEQ. ID. NO: 1 with leucine (T306L), substitution of the 346$^{th}$ glutamic acid of the M-MLV originated reverse transcriptase represented by SEQ. ID. NO: 1 with methionine (E346M), substitution of the 408$^{th}$ proline of the M-MLV originated reverse transcriptase represented by SEQ. ID. NO: 1 with glutamic acid (P408E), substitution of the 438$^{th}$ histidine of the M-MLV originated reverse transcriptase represented by SEQ. ID. NO: 1 with tyrosine (H438Y), and substitution of the 454$^{th}$ asparagin of the M-MLV originated reverse transcriptase represented by SEQ. ID. NO: 1 with phenylalanine (N454F) were constructed (see FIG. 1). To do so, mutation was induced in the gene represented by SEQ. ID. NO: 10 encoding the reverse transcriptase having the amino acid sequence represented by SEQ. ID. NO: 1 (see FIG. 2-FIG. 9). The said mutant gene has one of the nucleotide sequences each represented by SEQ. ID. NO: 11~NO: 18. The procedure of the construction of the said mutant gene is as follows:

To increase protein expression in *Escherichia coli*, gene sequence of the M-MLV reverse transcriptase represented by SEQ. ID. NO: 10 was optimized to fit codon usage of *E. coli*, and as a result, the nucleotide sequence represented by SEQ. ID. NO: 19 was obtained. Based on the optimized nucleotide sequence, wild type gene and K295Q mutant gene were synthesized. First, to obtain the nucleotide sequence of the wild type gene represented by SEQ. ID. NO: 19, sense and antisense strands were designed to have the annealing temperature of about 60° C. (20-40 bases). Then, the designed oligonucleotides were synthesized (Bioneer, Korea). The synthesized oligonucleotides had the nucleotide sequences each represented by SEQ. ID. NO: 20~NO: 149. Ligation of the synthesized oligonucleotides was induced by Kination-LCR (Korean Patent Application No. 2008-0025050) by repeated reaction at 40° C. and at 60° C., leading to the synthesis of double-stranded total gene having the nucleotide sequence represented by SEQ. ID. NO: 19. K295Q mutant gene was also constructed by the same manner as described above except that the nucleotide sequences each represented by SEQ. ID. NO: 150 and NO: 151 were used instead of those nucleotide sequences each represented by SEQ. ID. NO: 77 and NO: 78. The synthesized genes were heat-treated at 95° C. for 5 minutes, followed by reaction with the primers represented by SEQ. ID. NO: 152 and NO: 153 at 95° C. for 1 minute, at 65° C. for 1 minute, and at 72° C. for 2 minutes and 30 seconds. This reaction cycle was repeated 30 times and additional reaction was induced at 72° C. for 10 minutes to amplify the gene. The amplified gene was ligated in pGEM-T easy vector (Promega, USA), which was used for the transformation of E. coli DH5α (RBC, USA). As a result, wild type and K295Q mutant gene clones were obtained at a large scale.

Mutation was induced by site-directed mutagenesis by using the synthesized wild type gene as a template to produce mutations of Q63L, K264L, T306L, E346M, P408E, H438Y, and N454F. The site-directed mutagenesis was performed as follows: First, oligonucleotides having the nucleotide sequences each represented by SEQ. ID. NO: 154 NO: 167 were synthesized. The mutant gene was heat-treated at 95° C. for 5 minutes, followed by reaction with the synthesized oligonucleotides as primers and pfu DNA polymerase at 95° C. for 1 minute, at 65° C. for 1 minute, and at 72° C. for 5 minutes and 30 seconds. This reaction cycle was repeated 30 times and additional reaction was induced at 72° C. for 10 minutes to amplify the gene. The amplified mutant gene product was self-ligated by Kination-self ligation, which was used for the transformation of E. coli DH5α (RBC, USA). As a result, clones of Q63L, K264L, T306L, E346M, P408E, H438Y, and N454F mutant genes were obtained at a large scale.

Example 2

Mutant Gene Transformation

The 8 mutant reverse transcriptase genes constructed in Example 1 were cloned by using the extranuclear gens PET 22b(+) (NOVAGEN CO.) as an recombination vector. To do so, PCR was performed with the mutant genes (Q63L, K264L, T306L, and E346M) synthesized by being introduced in pGEM-T easy vector (Promega) using the following primer set.

```
Sense strand:
                                    (SEQ. ID. NO: 168)
5'-GCG CGC CAT ATG CTG AAC ATC GAA GAC GAA CAC CGT CTG CAC GAA AC-3' (Nde I)

Antisense strand:
                                    (SEQ. ID. NO: 169)
5'-GCG CGC GCG GCC GCT TAG ATC AGC AGG GTA GAG GTG TCC GGG GTT TC-3' (Not I)
```

PCR was also performed with other mutant genes (K295Q, P408E, H438Y, and N454Y) using the following primer set.

```
Sense strand:
                                    (SEQ. ID. NO: 170)
5'-GCG CGC CAT ATG CTG AAC ATC GAA GAC GAA CAC CGT CTG CAC GAA AC-3' (Nde I)

Antisense strand:
                                    (SEQ. ID. NO: 171)
5'-GCG CGC GCG GCC GCG ATC AGC AGG GTA GAG GTG TCC GGG GTT TC-3' (Not I)
```

The extranuclear gene vector PET 22b(+) and each M-MLV reverse transcriptase gene fragment obtained by PCR were digested with NdeI (5' end) and NotI (3' end). The digested fragments were purified by using gel extraction kit (BIONEER CO.). The fragments were reacted at 16° C. for 2 hours by using T4 DNA ligase (TAKARA CO.). Then, each mutant gene was inserted in the extranuclear gene vector PET 22b(+).

Escherichia coli DH5α was transformed with the extranuclear gene vector PET 22b(+) introduced with the mutant gene, and as a result recombinant host cells were prepared. The transformation herein was performed by the following steps: DH5α host cells frozen at −70° C. were thawed. The thawed host cells were mixed with 1 µg/µl of the DNA recombinant vector, which stood in ice for 30 minutes, followed by heat-treatment at 42° C. for 90 seconds. The heat-treated host cells were smeared on LB medium plate containing ampicillin (50 mg/ml), followed by culture at 37° C. for overnight. As a result, clones were obtained. Each gene sequence of the obtained clones was confirmed by using the primer set comprising the following nucleotide sequences. Each plasmid of the confirmed clones was introduced in BL21(DE3) host cells for transformation and then expression strains were obtained.

```
T7 promoter sense strand:
                                    (SEQ. ID. NO: 172)
5'-TAA TAC GAC TCA CTA TAG GG-3'

T7 terminator antisense strand:
                                    (SEQ. ID. NO: 173)
5'-GCT AGT TAT TGC TCA GCG G-3'
```

Example 3

Expression of Mutant Reverse Transcriptase

Single colony of the expression strain prepared by transforming BL21(DE3) host cells was taken and transferred in 15 ml of LB (Luria-Bertani) medium containing ampicillin (50 mg/ml), followed by culture at 37° C. for overnight. As a result, seed cells were obtained. The obtained seed cells were placed in 1 l of LB medium containing ampicillin, followed by culture at 37° C. for 2 hours, to which 0.5 mM IPTG (isopropyl β-D-1-thiogalactopyranoside) was added. Expression was induced for 2 more hours. The cultured cells were centrifuged and as a result pellet was obtained. The pellet was stored at −50° C. until the pellet was purified.

Example 4

Purification of Mutant Reverse Transcriptase 5 g of the frozen cell pellet obtained in Example 3 was pulverized, followed by suspension in lysis buffer (25 mM Tris-HCl (pH 7.6), 1 mM EDTA, 10% (v/v) β-mercaptoethanol, and phenylmethylsulfonyl fluoride (PMSF) 20 ml) for 30 minutes with stirring at 4° C. Then, the cells were lysed by using Fisher sonicator. The cell lysate was centrifuged at 11,000 rpm for 1 hour at 4° C., and pellet was discarded. The remaining clear lysate was dialyzed in a buffer (40 mM Tris-HCl (pH 7.6), 2 mM EDTA, 28.58 mM β-mercaptoethanol, and 100 mM KCl).

Example 5

Chromatography of Mutant Reverse Transcriptase

FPLC was performed to purify the mutant reverse transcriptase by using Amersham FPLC device. At that time, Amersham XK16 (1.6 cm×30.0 cm) was used as the first column. The column was filled with ion exchange resin column chromatography DEAE hyper-D (Pall Co.), which was washed with 250 ml of column buffer containing 1 M KCl. Then, 60 ml of bed equilibrated with buffer was obtained. 20 ml of the clear cell lysate was loaded to the column at the flow rate of 5 ml/min. Among the loaded lysate, those not absorbed on the column were taken and then applied to the next column. The obtained lysate was applied to the second chromatography. The column Amersham XK16 (1.6 cm×30.0 cm) was washed and equilibrated. The column was filled with affinity chromatography heparin hyper-D (Pall Co.). As a result, 50 ml of bed was obtained. The bed was equilibrated with buffer. The lysate was loaded to the column, followed by elution with 100~150 ml of 0.2 M~0.6 M KCl linear salt gradient of column buffer. The eluted lysate was applied to 26×60 S-200 gel filtration column (GE healthcare). As a result, high purity reverse transcriptase was obtained. The column fraction proceeded to SDS-polyacrylamide gel electrophoresis (SDS-PAGE), followed by Coomassie brilliant blue staining. 10 fi was taken from each fraction, which was analyzed on each gel lane. Protein having similar molecular weight of wild type (74 KDa) was collected. To secure the stability of the collected protein, the protein was dialyzed in conservative solution (20 mM Tris-HCl (pH 7.6), 0.1 mM EDTA, 150 mM NaCl, 0.1% IGEPAL CA-630 (Polyethoxyethanol) 1 mM DTT (Dithiothreitol), and 50% glycerol), and as a result the mutant enzyme was obtained and stored at −20° C.

Example 6

RT-PCR with Mutant Reverse Transcriptase

RT-PCR was performed to confirm the activity of the separated mutant reverse transcriptase. Ingredients used for RT-PCR were as follows, and the total RNA was used at the concentrations of 5 ng/µl~500, 50, and 5 pg/µl.
5× reaction buffer 4 µl (Bioneer Co.)
10 mM dNTP 2 µl
dT(18) 10 pmol 1 µl
100 mM DTT 2 µl
RNase inhibitor (50 ng/µl) 1 µl
DW 7 µl
Total RNA 2 µl For the comparative example, wild type reverse transcriptase was used for RT-PCR performed at 42° C., 50° C., 60° C., 65° C., and 70° C. (in the case of T306L, reaction at 37° C. was added) for 1 hour. The produced cDNA was used for PCR. The target gene for the amplification was GAPDH (500 bp) and the primer set having the nucleotide sequences presented below was used.

```
Sense strand:
                                (SEQ. ID. NO: 174)
5'-GAAGGTGAAGGTCGGAGTCAACG-3'

Antisense strand:
                                (SEQ. ID. NO: 175)
5'-AGTCCTTCCACGATACCAAAGTTG-3'
```

Preparation having the below composition was used:
PCR premix type (Bioneer)
Sense primer: 5 pmol, 1 µl
Antisense primer: 5 pmol, 1 µl
DW 13 µl
cDNA 5 µl PCR was performed as follows: 95° C. for 30 seconds, 57° C. for 30 seconds, and 72° C. for 30 seconds (30 cycles). The PCR product proceeded to agarose gel electrophoresis to confirm the amplified product.

Figure 11:
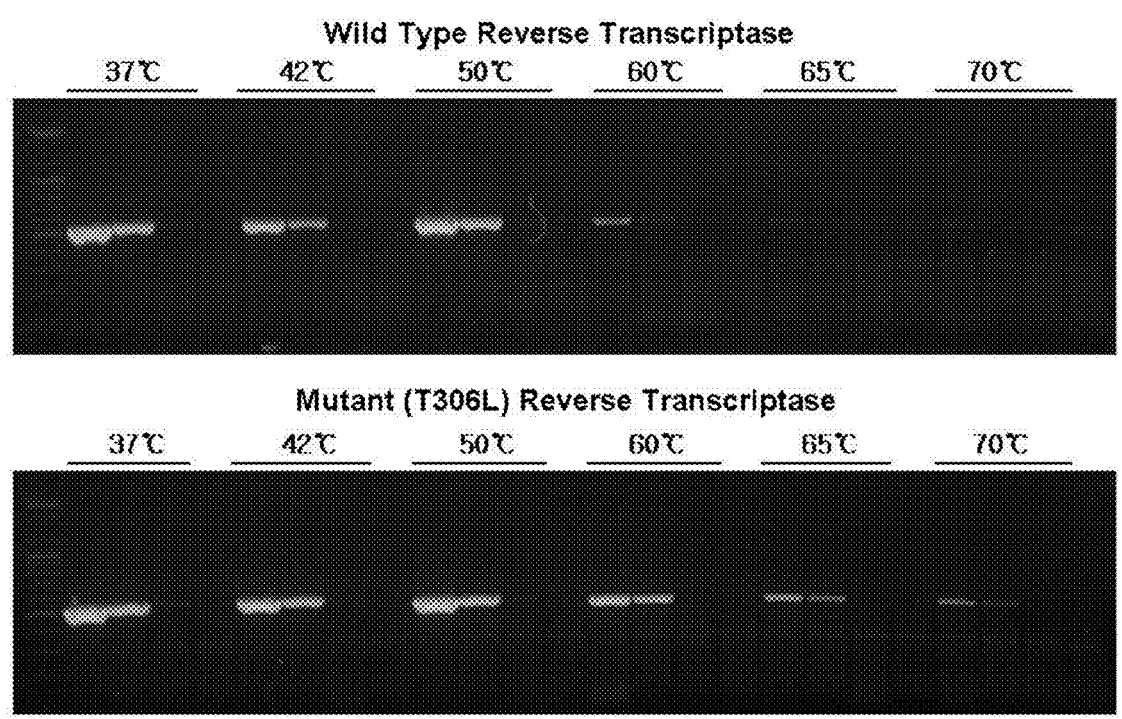
FIG. 11 is a set of electrophoresis photographs showing the results of reverse transcription induced by using the wild type reverse transcriptase (SEQ. ID. NO: 1) and the T306L mutant reverse transcriptase of the present invention (SEQ. ID. NO: 5) at 37° C., at 42° C., at 50° C., at 60° C., at 65° C., and at 70° C.

As a result, the wild type M-MLV originated mutant reverse transcriptase of the present invention demonstrated higher thermostability than the wild type reverse transcriptase. In particular, K295Q, T306L, and P408E mutant reverse transcriptases showed excellent thermostability. The wild type M-MLV reverse transcriptase did not show activity at 60° C., while K295Q, T306L, and P408E mutant reverse transcriptases maintained reverse transcription activity at the reaction temperature reaching 60° C. (FIG. 10). T306L mutant reverse transcriptase showing the highest thermostability demonstrated equal thermostability to the wild type M-MLV reverse transcriptase at 37° C., 42° C., and at 50° C., but showed much higher thermostability than the wild type M-MLV reverse transcriptase at 60° C., 65° C., and at 70° C. (FIG. 11).

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A reverse transcriptase having improved thermostability by substitution of the 306$^{th}$ threonine with leucine (T306L) of the amino acid sequence of M-MLV originated reverse transcriptase of SEQ ID NO: 1.

2. A reverse transcriptase having improved thermostability by substitution of the 306$^{th}$ threonine with leucine (T306L) of the amino acid sequence of M-MLV originated reverse transcriptase of SEQ ID NO: 1, wherein the reverse transcriptase further comprises one or more amino acid substitutions selected from the group consisting of substitution of the 63$^{rd}$ glutamine of the wild type reverse transcriptase of SEQ ID NO: 1 with leucine (Q63L), substitution of the 264$^{th}$ lysine with leucine (K264L), substitution of the 295$^{th}$ lysine with glutamine (K295Q), substitution of the 346$^{th}$ glutamic acid with methionine (E346M), substitution of the 408$^{th}$ proline with glutamic acid (P408E), substitution of the 438$^{th}$ histidine with tyrosine (H438Y), and substitution of the 454$^{th}$ asparagin with phenylalanine (N454F).

3. The reverse transcriptase according to claim 1, wherein the reverse transcriptase demonstrates higher reverse transcription activity at the reaction temperature of 60° C.~70° C. than the wild type M-MLV reverse transcriptase having the amino acid sequence of SEQ ID NO: 1.

4. A gene encoding the reverse transcriptase having improved thermostability of claim 1 or claim 2.

5. The gene encoding the reverse transcriptase according to claim 4, wherein the gene has the nucleotide sequence of SEQ ID NO: 14.

6. An expression vector comprising the gene of claim 4.

7. A transformant transformed with the expression vector of claim 6.

8. A kit for reverse transcription comprising the reverse transcriptase having improved thermostability of claim 1.

9. The reverse transcriptase according to claim 2, wherein the reverse transcriptase demonstrates higher reverse transcription activity at the reaction temperature of 60° C.~70° C. than the wild type M-MLV reverse transcriptase having the amino acid sequence of SEQ ID NO: 1.

* * * * *

SEQUENCE LISTING

<160> NUMBER OF SEQ ID NOS: 175

<210> SEQ ID NO 1
<211> LENGTH: 672
<212> TYPE: PRT
<213> ORGANISM: Moloney Murine Leukemia Virus

<400> SEQUENCE: 1

```
Met Leu Asn Ile Glu Asp Glu His Arg Leu His Glu Thr Ser Lys Glu
  1               5                  10                  15
Pro Asp Val Ser Leu Gly Ser Thr Trp Leu Ser Asp Phe Pro Gln Ala
                 20                  25                  30
Trp Ala Glu Thr Gly Gly Met Gly Leu Ala Val Arg Gln Ala Pro Leu
             35                  40                  45
Ile Ile Pro Leu Lys Ala Thr Ser Thr Pro Val Ser Ile Lys Gln Tyr
         50                  55                  60
Pro Met Ser Gln Glu Ala Arg Leu Gly Ile Lys Pro His Ile Gln Arg
 65                  70                  75                  80
Leu Leu Asp Gln Gly Ile Leu Val Pro Cys Gln Ser Pro Trp Asn Thr
                 85                  90                  95
Pro Leu Leu Pro Val Lys Lys Pro Gly Thr Asn Asp Tyr Arg Pro Val
                100                 105                 110
Gln Asp Leu Arg Glu Val Asn Lys Arg Val Glu Asp Ile His Pro Thr
            115                 120                 125
Val Pro Asn Pro Tyr Asn Leu Leu Ser Gly Leu Pro Pro Ser His Gln
        130                 135                 140
Trp Tyr Thr Val Leu Asp Leu Lys Asp Ala Phe Phe Cys Leu Arg Leu
145                 150                 155                 160
His Pro Thr Ser Gln Pro Leu Phe Ala Phe Glu Trp Arg Asp Pro Glu
                165                 170                 175
Met Gly Ile Ser Gly Gln Leu Thr Trp Thr Arg Leu Pro Gln Gly Phe
            180                 185                 190
Lys Asn Ser Pro Thr Leu Phe Asp Glu Ala Leu His Arg Asp Leu Ala
        195                 200                 205
Asp Phe Arg Ile Gln His Pro Asp Leu Ile Leu Leu Gln Tyr Val Asp
    210                 215                 220
Asp Leu Leu Leu Ala Ala Thr Ser Glu Leu Asp Cys Gln Gln Gly Thr
225                 230                 235                 240
Arg Ala Leu Leu Gln Thr Leu Gly Asn Leu Gly Tyr Arg Ala Ser Ala
                245                 250                 255
Lys Lys Ala Gln Ile Cys Gln Lys Gln Val Lys Tyr Leu Gly Tyr Leu
            260                 265                 270
Leu Lys Glu Gly Gln Arg Trp Leu Thr Glu Ala Arg Lys Glu Thr Val
        275                 280                 285
Met Gly Gln Pro Thr Pro Lys Thr Pro Arg Gln Leu Arg Glu Phe Leu
    290                 295                 300
Gly Thr Ala Gly Phe Cys Arg Leu Trp Ile Pro Gly Phe Ala Glu Met
305                 310                 315                 320
Ala Ala Pro Leu Tyr Pro Leu Thr Lys Thr Gly Thr Leu Phe Asn Trp
                325                 330                 335
Gly Pro Asp Gln Gln Lys Ala Tyr Gln Glu Ile Lys Gln Ala Leu Leu
            340                 345                 350
Thr Ala Pro Ala Leu Gly Leu Pro Asp Leu Thr Lys Pro Phe Glu Leu
        355                 360                 365
Phe Val Asp Glu Lys Gln Gly Tyr Ala Lys Gly Val Leu Thr Gln Lys
    370                 375                 380
Leu Gly Pro Trp Arg Arg Pro Val Ala Tyr Leu Ser Lys Lys Leu Asp
385                 390                 395                 400
Pro Val Ala Ala Gly Trp Pro Pro Cys Leu Arg Met Val Ala Ala Ile
                405                 410                 415
Ala Val Leu Thr Lys Asp Ala Gly Lys Leu Thr Met Gly Gln Pro Leu
```

```
                420             425             430
Val Ile Leu Ala Pro His Ala Val Glu Ala Leu Val Lys Gln Pro Pro
            435                 440                 445

Asp Arg Trp Leu Ser Asn Ala Arg Met Thr His Tyr Gln Ala Leu Leu
        450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
            485                 490                 495

Asp Ile Leu Ala Glu Ala His Gly Thr Arg Pro Asp Leu Thr Asp Gln
        500                 505                 510

Pro Leu Pro Asp Ala Asp His Thr Trp Tyr Thr Asp Gly Ser Ser Leu
            515                 520                 525

Leu Gln Glu Gly Gln Arg Lys Ala Gly Ala Ala Val Thr Thr Glu Thr
        530                 535                 540

Glu Val Ile Trp Ala Lys Ala Leu Pro Ala Gly Thr Ser Ala Gln Arg
545                 550                 555                 560

Ala Glu Leu Ile Ala Leu Thr Gln Ala Leu Lys Met Ala Glu Gly Lys
            565                 570                 575

Lys Leu Asn Val Tyr Thr Asp Ser Arg Tyr Ala Phe Ala Thr Ala His
        580                 585                 590

Ile His Gly Glu Ile Tyr Arg Arg Arg Gly Leu Leu Thr Ser Glu Gly
            595                 600                 605

Lys Glu Ile Lys Asn Lys Asp Glu Ile Leu Ala Leu Leu Lys Ala Leu
        610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
            645                 650                 655

Arg Lys Ala Ala Ile Thr Glu Thr Pro Asp Thr Ser Thr Leu Leu Ile
        660                 665                 670

<210> SEQ ID NO 2
<211> LENGTH: 672
<212> TYPE: PRT
<213> ORGANISM: Moloney Murine Leukemia Virus
<220> FEATURE:
<221> NAME/KEY: MUTAGEN
<222> LOCATION: (63)
<223> OTHER INFORMATION: mutant reverse transcriptase having leucine
      residue instead of glutamine residue at 63 position of SEQ. ID.
      No: 1

<400> SEQUENCE: 2

Met Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
            20                  25                  30

Trp Ala Glu Thr Gly Gly Met Gly Leu Ala Val Arg Gln Ala Pro Leu
        35                  40                  45

Ile Ile Pro Leu Lys Ala Thr Ser Thr Pro Val Ser Ile Lys Leu Tyr
    50                  55                  60

Pro Met Ser Gln Glu Ala Arg Leu Gly Ile Lys Pro His Ile Gln Arg
65                  70                  75                  80

Leu Leu Asp Gln Gly Ile Leu Val Pro Cys Gln Ser Pro Trp Asn Thr
            85                  90                  95
```

```
Pro Leu Leu Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Gly Leu Pro Pro Ser His Gln
    130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190

Lys Asn Ser Pro Thr Leu Phe Asp Glu Ala Leu His Arg Asp Leu Ala
        195                 200                 205

Asp Phe Arg Ile Gln His Pro Asp Leu Ile Leu Leu Gln Tyr Val Asp
    210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Leu Thr Glu Ala Arg Lys Glu Thr Val
        275                 280                 285

Met Gly Gln Pro Thr Pro Lys Thr Pro Arg Gln Leu Arg Glu Phe Leu
    290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Thr Leu Phe Asn Trp
                325                 330                 335

Gly Pro Asp Gln Gln Lys Ala Tyr Gln Glu Ile Lys Gln Ala Leu Leu
            340                 345                 350

Thr Ala Pro Ala Leu Gly Leu Pro Asp Leu Thr Lys Pro Phe Glu Leu
        355                 360                 365

Phe Val Asp Glu Lys Gln Gly Tyr Ala Lys Gly Val Leu Thr Gln Lys
    370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
            420                 425                 430

Val Ile Leu Ala Pro His Ala Val Glu Ala Leu Val Lys Gln Pro Pro
        435                 440                 445

Asp Arg Trp Leu Ser Asn Ala Arg Met Thr His Tyr Gln Ala Leu Leu
    450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
            500                 505                 510

Pro Leu Pro Asp Ala Asp His Thr Trp Tyr Thr Asp Gly Ser Ser Leu
```

```
            515                 520                 525
Leu Gln Glu Gly Gln Arg Lys Ala Gly Ala Val Thr Thr Glu Thr
    530                 535                 540

Glu Val Ile Trp Ala Lys Ala Leu Pro Ala Gly Thr Ser Ala Gln Arg
545                 550                 555                 560

Ala Glu Leu Ile Ala Leu Thr Gln Ala Leu Lys Met Ala Glu Gly Lys
                565                 570                 575

Lys Leu Asn Val Tyr Thr Asp Ser Arg Tyr Ala Phe Ala Thr Ala His
                580                 585                 590

Ile His Gly Glu Ile Tyr Arg Arg Gly Leu Leu Thr Ser Glu Gly
                595                 600                 605

Lys Glu Ile Lys Asn Lys Asp Glu Ile Leu Ala Leu Leu Lys Ala Leu
            610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
                645                 650                 655

Arg Lys Ala Ala Ile Thr Glu Thr Pro Asp Thr Ser Thr Leu Leu Ile
            660                 665                 670

<210> SEQ ID NO 3
<211> LENGTH: 672
<212> TYPE: PRT
<213> ORGANISM: Moloney Murine Leukemia Virus
<220> FEATURE:
<221> NAME/KEY: MUTAGEN
<222> LOCATION: (264)
<223> OTHER INFORMATION: mutant reverse transcriptase having leucine
      residue instead of lysine residue at 264 position of SEQ. ID.
      No: 1

<400> SEQUENCE: 3

Met Leu Asn Ile Glu Asp Glu His Arg Leu His Glu Thr Ser Lys Glu
  1               5                  10                  15

Pro Asp Val Ser Leu Gly Ser Thr Trp Leu Ser Asp Phe Pro Gln Ala
                20                  25                  30

Trp Ala Glu Thr Gly Gly Met Gly Leu Ala Val Arg Gln Ala Pro Leu
            35                  40                  45

Ile Ile Pro Leu Lys Ala Thr Ser Thr Pro Val Ser Ile Lys Gln Tyr
    50                  55                  60

Pro Met Ser Gln Glu Ala Arg Leu Gly Ile Lys Pro His Ile Gln Arg
 65                 70                  75                  80

Leu Leu Asp Gln Gly Ile Leu Val Pro Cys Gln Ser Pro Trp Asn Thr
                85                  90                  95

Pro Leu Leu Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Gly Leu Pro Pro Ser His Gln
    130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190
```

```
Lys Asn Ser Pro Thr Leu Phe Asp Glu Ala Leu His Arg Asp Leu Ala
            195                 200                 205

Asp Phe Arg Ile Gln His Pro Asp Leu Ile Leu Leu Gln Tyr Val Asp
210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Leu Gln Val Lys Tyr Leu Gly Tyr Leu
            260                 265                 270

Leu Lys Glu Gly Gln Arg Trp Leu Thr Glu Ala Arg Lys Glu Thr Val
        275                 280                 285

Met Gly Gln Pro Thr Pro Lys Thr Pro Arg Gln Leu Arg Glu Phe Leu
    290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Thr Leu Phe Asn Trp
                325                 330                 335

Gly Pro Asp Gln Gln Lys Ala Tyr Gln Glu Ile Lys Gln Ala Leu Leu
            340                 345                 350

Thr Ala Pro Ala Leu Gly Leu Pro Asp Leu Thr Lys Pro Phe Glu Leu
        355                 360                 365

Phe Val Asp Glu Lys Gln Gly Tyr Ala Lys Gly Val Leu Thr Gln Lys
    370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
            420                 425                 430

Val Ile Leu Ala Pro His Ala Val Glu Ala Leu Val Lys Gln Pro Pro
        435                 440                 445

Asp Arg Trp Leu Ser Asn Ala Arg Met Thr His Tyr Gln Ala Leu Leu
    450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
            500                 505                 510

Pro Leu Pro Asp Ala Asp His Thr Trp Tyr Thr Asp Gly Ser Ser Leu
        515                 520                 525

Leu Gln Glu Gly Gln Arg Lys Ala Gly Ala Ala Val Thr Thr Glu Thr
    530                 535                 540

Glu Val Ile Trp Ala Lys Ala Leu Pro Ala Gly Thr Ser Ala Gln Arg
545                 550                 555                 560

Ala Glu Leu Ile Ala Leu Thr Gln Ala Leu Lys Met Ala Glu Gly Lys
                565                 570                 575

Lys Leu Asn Val Tyr Thr Asp Ser Arg Tyr Ala Phe Ala Thr Ala His
            580                 585                 590

Ile His Gly Glu Ile Tyr Arg Arg Gly Leu Leu Thr Ser Glu Gly
        595                 600                 605

Lys Glu Ile Lys Asn Lys Asp Glu Ile Leu Ala Leu Leu Lys Ala Leu
```

-continued

```
                610                 615                 620
Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
                645                 650                 655

Arg Lys Ala Ala Ile Thr Glu Thr Pro Asp Thr Ser Thr Leu Leu Ile
                660                 665                 670

<210> SEQ ID NO 4
<211> LENGTH: 672
<212> TYPE: PRT
<213> ORGANISM: Moloney Murine Leukemia Virus
<220> FEATURE:
<221> NAME/KEY: MUTAGEN
<222> LOCATION: (295)
<223> OTHER INFORMATION: mutant reverse transcriptase having glutamine
      residue instead of lysine residue at 295 position of SEQ. ID.
      No: 1

<400> SEQUENCE: 4

Met Leu Asn Ile Glu Asp Glu His Arg Leu His Glu Thr Ser Lys Glu
  1               5                  10                  15

Pro Asp Val Ser Leu Gly Ser Thr Trp Leu Ser Asp Phe Pro Gln Ala
                 20                  25                  30

Trp Ala Glu Thr Gly Gly Met Gly Leu Ala Val Arg Gln Ala Pro Leu
             35                  40                  45

Ile Ile Pro Leu Lys Ala Thr Ser Thr Pro Val Ser Ile Lys Gln Tyr
         50                  55                  60

Pro Met Ser Gln Glu Ala Arg Leu Gly Ile Lys Pro His Ile Gln Arg
 65                  70                  75                  80

Leu Leu Asp Gln Gly Ile Leu Val Pro Cys Gln Ser Pro Trp Asn Thr
                 85                  90                  95

Pro Leu Leu Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Gly Leu Pro Pro Ser His Gln
    130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190

Lys Asn Ser Pro Thr Leu Phe Asp Glu Ala Leu His Arg Asp Leu Ala
        195                 200                 205

Asp Phe Arg Ile Gln His Pro Asp Leu Ile Leu Leu Gln Tyr Val Asp
    210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Leu Thr Glu Ala Arg Lys Glu Thr Val
        275                 280                 285
```

```
Met Gly Gln Pro Thr Pro Gln Thr Pro Arg Gln Leu Arg Glu Phe Leu
290                 295                 300
Gly Thr Ala Gly Phe Cys Arg Leu Trp Ile Pro Gly Phe Ala Glu Met
305                 310                 315                 320
Ala Ala Pro Leu Tyr Pro Leu Thr Lys Thr Gly Thr Leu Phe Asn Trp
                325                 330                 335
Gly Pro Asp Gln Gln Lys Ala Tyr Gln Glu Ile Lys Gln Ala Leu Leu
                340                 345                 350
Thr Ala Pro Ala Leu Gly Leu Pro Asp Leu Thr Lys Pro Phe Glu Leu
                355                 360                 365
Phe Val Asp Glu Lys Gln Gly Tyr Ala Lys Gly Val Leu Thr Gln Lys
370                 375                 380
Leu Gly Pro Trp Arg Arg Pro Val Ala Tyr Leu Ser Lys Lys Leu Asp
385                 390                 395                 400
Pro Val Ala Ala Gly Trp Pro Pro Cys Leu Arg Met Val Ala Ala Ile
                405                 410                 415
Ala Val Leu Thr Lys Asp Ala Gly Lys Leu Thr Met Gly Gln Pro Leu
                420                 425                 430
Val Ile Leu Ala Pro His Ala Val Glu Ala Leu Val Lys Gln Pro Pro
                435                 440                 445
Asp Arg Trp Leu Ser Asn Ala Arg Met Thr His Tyr Gln Ala Leu Leu
                450                 455                 460
Leu Asp Thr Asp Arg Val Gln Phe Gly Pro Val Val Ala Leu Asn Pro
465                 470                 475                 480
Ala Thr Leu Leu Pro Leu Pro Glu Glu Gly Leu Gln His Asn Cys Leu
                485                 490                 495
Asp Ile Leu Ala Glu Ala His Gly Thr Arg Pro Asp Leu Thr Asp Gln
                500                 505                 510
Pro Leu Pro Asp Ala Asp His Thr Trp Tyr Thr Asp Gly Ser Ser Leu
                515                 520                 525
Leu Gln Glu Gly Gln Arg Lys Ala Gly Ala Ala Val Thr Thr Glu Thr
                530                 535                 540
Glu Val Ile Trp Ala Lys Ala Leu Pro Ala Gly Thr Ser Ala Gln Arg
545                 550                 555                 560
Ala Glu Leu Ile Ala Leu Thr Gln Ala Leu Lys Met Ala Glu Gly Lys
                565                 570                 575
Lys Leu Asn Val Tyr Thr Asp Ser Arg Tyr Ala Phe Ala Thr Ala His
                580                 585                 590
Ile His Gly Glu Ile Tyr Arg Arg Gly Leu Leu Thr Ser Glu Gly
                595                 600                 605
Lys Glu Ile Lys Asn Lys Asp Glu Ile Leu Ala Leu Leu Lys Ala Leu
                610                 615                 620
Phe Leu Pro Lys Arg Leu Ser Ile Ile His Cys Pro Gly His Gln Lys
625                 630                 635                 640
Gly His Ser Ala Glu Ala Arg Gly Asn Arg Met Ala Asp Gln Ala Ala
                645                 650                 655
Arg Lys Ala Ala Ile Thr Glu Thr Pro Asp Thr Ser Thr Leu Leu Ile
                660                 665                 670

<210> SEQ ID NO 5
<211> LENGTH: 672
<212> TYPE: PRT
<213> ORGANISM: Moloney Murine Leukemia Virus
<220> FEATURE:
<221> NAME/KEY: MUTAGEN
```

<222> LOCATION: (306)
<223> OTHER INFORMATION: mutant reverse transcriptase having leucine
    residue instead of threonine residue at 306 position of SEQ. ID.
    No: 1

<400> SEQUENCE: 5

```
Met Leu Asn Ile Glu Asp Glu His Arg Leu His Glu Thr Ser Lys Glu
 1               5                  10                  15

Pro Asp Val Ser Leu Gly Ser Thr Trp Leu Ser Asp Phe Pro Gln Ala
             20                  25                  30

Trp Ala Glu Thr Gly Gly Met Gly Leu Ala Val Arg Gln Ala Pro Leu
         35                  40                  45

Ile Ile Pro Leu Lys Ala Thr Ser Thr Pro Val Ser Ile Lys Gln Tyr
     50                  55                  60

Pro Met Ser Gln Glu Ala Arg Leu Gly Ile Lys Pro His Ile Gln Arg
 65                  70                  75                  80

Leu Leu Asp Gln Gly Ile Leu Val Pro Cys Gln Ser Pro Trp Asn Thr
                 85                  90                  95

Pro Leu Leu Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Gly Leu Pro Pro Ser His Gln
130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190

Lys Asn Ser Pro Thr Leu Phe Asp Glu Ala Leu His Arg Asp Leu Ala
        195                 200                 205

Asp Phe Arg Ile Gln His Pro Asp Leu Ile Leu Leu Gln Tyr Val Asp
    210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Leu Thr Glu Ala Arg Lys Glu Thr Val
        275                 280                 285

Met Gly Gln Pro Thr Pro Lys Thr Pro Arg Gln Leu Arg Glu Phe Leu
    290                 295                 300

Gly Leu Ala Gly Phe Cys Arg Leu Trp Ile Pro Gly Phe Ala Glu Met
305                 310                 315                 320

Ala Ala Pro Leu Tyr Pro Leu Thr Lys Thr Gly Thr Leu Phe Asn Trp
                325                 330                 335

Gly Pro Asp Gln Gln Lys Ala Tyr Gln Glu Ile Lys Gln Ala Leu Leu
            340                 345                 350

Thr Ala Pro Ala Leu Gly Leu Pro Asp Leu Thr Lys Pro Phe Glu Leu
        355                 360                 365

Phe Val Asp Glu Lys Gln Gly Tyr Ala Lys Gly Val Leu Thr Gln Lys
    370                 375                 380
```

```
Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
            405                 410                 415

Ala Val Leu Thr Lys Asp Ala Gly Lys Leu Thr Met Gly Gln Pro Leu
            420                 425                 430

Val Ile Leu Ala Pro His Ala Val Glu Ala Leu Val Lys Gln Pro Pro
            435                 440                 445

Asp Arg Trp Leu Ser Asn Ala Arg Met Thr His Tyr Gln Ala Leu Leu
    450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
            500                 505                 510

Pro Leu Pro Asp Ala Asp His Thr Trp Tyr Thr Asp Gly Ser Ser Leu
            515                 520                 525

Leu Gln Glu Gly Gln Arg Lys Ala Gly Ala Ala Val Thr Thr Glu Thr
530                 535                 540

Glu Val Ile Trp Ala Lys Ala Leu Pro Ala Gly Thr Ser Ala Gln Arg
545                 550                 555                 560

Ala Glu Leu Ile Ala Leu Thr Gln Ala Leu Lys Met Ala Glu Gly Lys
                565                 570                 575

Lys Leu Asn Val Tyr Thr Asp Ser Arg Tyr Ala Phe Ala Thr Ala His
            580                 585                 590

Ile His Gly Glu Ile Tyr Arg Arg Arg Gly Leu Leu Thr Ser Glu Gly
            595                 600                 605

Lys Glu Ile Lys Asn Lys Asp Glu Ile Leu Ala Leu Leu Lys Ala Leu
610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
                645                 650                 655

Arg Lys Ala Ala Ile Thr Glu Thr Pro Asp Thr Ser Thr Leu Leu Ile
            660                 665                 670

<210> SEQ ID NO 6
<211> LENGTH: 672
<212> TYPE: PRT
<213> ORGANISM: Moloney Murine Leukemia Virus
<220> FEATURE:
<221> NAME/KEY: MUTAGEN
<222> LOCATION: (346)
<223> OTHER INFORMATION: mutant reverse transcriptase having methionine
      residue instead of glutamic acid residue at 346 position of SEQ.
      ID. No: 1

<400> SEQUENCE: 6

Met Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
            20                  25                  30

Trp Ala Glu Thr Gly Gly Met Gly Leu Ala Val Arg Gln Ala Pro Leu
        35                  40                  45

Ile Ile Pro Leu Lys Ala Thr Ser Thr Pro Val Ser Ile Lys Gln Tyr
    50                  55                  60
```

```
Pro Met Ser Gln Glu Ala Arg Leu Gly Ile Lys Pro His Ile Gln Arg
 65                  70                  75                  80

Leu Leu Asp Gln Gly Ile Leu Val Pro Cys Gln Ser Pro Trp Asn Thr
                 85                  90                  95

Pro Leu Leu Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
            115                 120                 125

Val Pro Asn Pro Tyr Asn Leu Leu Ser Gly Leu Pro Pro Ser His Gln
130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
                180                 185                 190

Lys Asn Ser Pro Thr Leu Phe Asp Glu Ala Leu His Arg Asp Leu Ala
                195                 200                 205

Asp Phe Arg Ile Gln His Pro Asp Leu Ile Leu Leu Gln Tyr Val Asp
210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
                260                 265                 270

Leu Lys Glu Gly Gln Arg Trp Leu Thr Glu Ala Arg Lys Glu Thr Val
                275                 280                 285

Met Gly Gln Pro Thr Pro Lys Thr Pro Arg Gln Leu Arg Glu Phe Leu
    290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Thr Leu Phe Asn Trp
                325                 330                 335

Gly Pro Asp Gln Gln Lys Ala Tyr Gln Met Ile Lys Gln Ala Leu Leu
                340                 345                 350

Thr Ala Pro Ala Leu Gly Leu Pro Asp Leu Thr Lys Pro Phe Glu Leu
                355                 360                 365

Phe Val Asp Glu Lys Gln Gly Tyr Ala Lys Gly Val Leu Thr Gln Lys
                370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
                420                 425                 430

Val Ile Leu Ala Pro His Ala Val Glu Ala Leu Val Lys Gln Pro Pro
                435                 440                 445

Asp Arg Trp Leu Ser Asn Ala Arg Met Thr His Tyr Gln Ala Leu Leu
                450                 455                 460

Leu Asp Thr Asp Arg Val Gln Phe Gly Pro Val Val Ala Leu Asn Pro
465                 470                 475                 480
```

```
Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
            500                 505                 510

Pro Leu Pro Asp Ala Asp His Thr Trp Tyr Thr Asp Gly Ser Ser Leu
            515                 520                 525

Leu Gln Glu Gly Gln Arg Lys Ala Gly Ala Ala Val Thr Thr Glu Thr
        530                 535                 540

Glu Val Ile Trp Ala Lys Ala Leu Pro Ala Gly Thr Ser Ala Gln Arg
545                 550                 555                 560

Ala Glu Leu Ile Ala Leu Thr Gln Ala Leu Lys Met Ala Glu Gly Lys
                565                 570                 575

Lys Leu Asn Val Tyr Thr Asp Ser Arg Tyr Ala Phe Ala Thr Ala His
            580                 585                 590

Ile His Gly Glu Ile Tyr Arg Arg Arg Gly Leu Leu Thr Ser Glu Gly
            595                 600                 605

Lys Glu Ile Lys Asn Lys Asp Glu Ile Leu Ala Leu Leu Lys Ala Leu
        610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
                645                 650                 655

Arg Lys Ala Ala Ile Thr Glu Thr Pro Asp Thr Ser Thr Leu Leu Ile
            660                 665                 670

<210> SEQ ID NO 7
<211> LENGTH: 672
<212> TYPE: PRT
<213> ORGANISM: Moloney Murine Leukemia Virus
<220> FEATURE:
<221> NAME/KEY: MUTAGEN
<222> LOCATION: (408)
<223> OTHER INFORMATION: mutant reverse transcriptase having glutamic
      acid residue instead of proline residue at 408 position of SEQ.
      ID. No: 1

<400> SEQUENCE: 7

Met Leu Asn Ile Glu Asp Glu His Arg Leu His Glu Thr Ser Lys Glu
 1               5                  10                  15

Pro Asp Val Ser Leu Gly Ser Thr Trp Leu Ser Asp Phe Pro Gln Ala
             20                  25                  30

Trp Ala Glu Thr Gly Gly Met Gly Leu Ala Val Arg Gln Ala Pro Leu
         35                  40                  45

Ile Ile Pro Leu Lys Ala Thr Ser Thr Pro Val Ser Ile Lys Gln Tyr
     50                  55                  60

Pro Met Ser Gln Glu Ala Arg Leu Gly Ile Lys Pro His Ile Gln Arg
 65                  70                  75                  80

Leu Leu Asp Gln Gly Ile Leu Val Pro Cys Gln Ser Pro Trp Asn Thr
                 85                  90                  95

Pro Leu Leu Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Gly Leu Pro Pro Ser His Gln
    130                 135                 140

Trp Tyr Thr Val Leu Asp Leu Lys Asp Ala Phe Phe Cys Leu Arg Leu
145                 150                 155                 160
```

-continued

His Pro Thr Ser Gln Pro Leu Phe Ala Phe Glu Trp Arg Asp Pro Glu
            165                 170                 175

Met Gly Ile Ser Gly Gln Leu Thr Trp Thr Arg Leu Pro Gln Gly Phe
            180                 185                 190

Lys Asn Ser Pro Thr Leu Phe Asp Glu Ala Leu His Arg Asp Leu Ala
            195                 200                 205

Asp Phe Arg Ile Gln His Pro Asp Leu Ile Leu Leu Gln Tyr Val Asp
        210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Leu Thr Glu Ala Arg Lys Glu Thr Val
        275                 280                 285

Met Gly Gln Pro Thr Pro Lys Thr Pro Arg Gln Leu Arg Glu Phe Leu
        290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Thr Leu Phe Asn Trp
                325                 330                 335

Gly Pro Asp Gln Gln Lys Ala Tyr Gln Glu Ile Lys Gln Ala Leu Leu
            340                 345                 350

Thr Ala Pro Ala Leu Gly Leu Pro Asp Leu Thr Lys Pro Phe Glu Leu
            355                 360                 365

Phe Val Asp Glu Lys Gln Gly Tyr Ala Lys Gly Val Leu Thr Gln Lys
        370                 375                 380

Leu Gly Pro Trp Arg Arg Pro Val Ala Tyr Leu Ser Lys Lys Leu Asp
385                 390                 395                 400

Pro Val Ala Ala Gly Trp Pro Glu Cys Leu Arg Met Val Ala Ala Ile
                405                 410                 415

Ala Val Leu Thr Lys Asp Ala Gly Lys Leu Thr Met Gly Gln Pro Leu
            420                 425                 430

Val Ile Leu Ala Pro His Ala Val Glu Ala Leu Val Lys Gln Pro Pro
        435                 440                 445

Asp Arg Trp Leu Ser Asn Ala Arg Met Thr His Tyr Gln Ala Leu Leu
        450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
            500                 505                 510

Pro Leu Pro Asp Ala Asp His Thr Trp Tyr Thr Asp Gly Ser Ser Leu
        515                 520                 525

Leu Gln Glu Gly Gln Arg Lys Ala Gly Ala Ala Val Thr Thr Glu Thr
        530                 535                 540

Glu Val Ile Trp Ala Lys Ala Leu Pro Ala Gly Thr Ser Ala Gln Arg
545                 550                 555                 560

Ala Glu Leu Ile Ala Leu Thr Gln Ala Leu Lys Met Ala Glu Gly Lys
                565                 570                 575

```
Lys Leu Asn Val Tyr Thr Asp Ser Arg Tyr Ala Phe Ala Thr Ala His
            580                 585                 590

Ile His Gly Glu Ile Tyr Arg Arg Gly Leu Leu Thr Ser Glu Gly
        595                 600                 605

Lys Glu Ile Lys Asn Lys Asp Glu Ile Leu Ala Leu Leu Lys Ala Leu
610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
                645                 650                 655

Arg Lys Ala Ala Ile Thr Glu Thr Pro Asp Thr Ser Thr Leu Leu Ile
            660                 665                 670
```

<210> SEQ ID NO 8
<211> LENGTH: 672
<212> TYPE: PRT
<213> ORGANISM: Moloney Murine Leukemia Virus
<220> FEATURE:
<221> NAME/KEY: MUTAGEN
<222> LOCATION: (438)
<223> OTHER INFORMATION: mutant reverse transcriptase having tyrosine
      residue instead of histidine residue at 438 position of SEQ. ID.
      No: 1

<400> SEQUENCE: 8

```
Met Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
            20                  25                  30

Trp Ala Glu Thr Gly Gly Met Gly Leu Ala Val Arg Gln Ala Pro Leu
        35                  40                  45

Ile Ile Pro Leu Lys Ala Thr Ser Thr Pro Val Ser Ile Lys Gln Tyr
    50                  55                  60

Pro Met Ser Gln Glu Ala Arg Leu Gly Ile Lys Pro His Ile Gln Arg
65                  70                  75                  80

Leu Leu Asp Gln Gly Ile Leu Val Pro Cys Gln Ser Pro Trp Asn Thr
                85                  90                  95

Pro Leu Leu Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Gly Leu Pro Pro Ser His Gln
130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190

Lys Asn Ser Pro Thr Leu Phe Asp Glu Ala Leu His Arg Asp Leu Ala
        195                 200                 205

Asp Phe Arg Ile Gln His Pro Asp Leu Ile Leu Leu Gln Tyr Val Asp
210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255
```

```
Lys Lys Ala Gln Ile Cys Gln Lys Gln Val Lys Tyr Leu Gly Tyr Leu
            260                 265                 270

Leu Lys Glu Gly Gln Arg Trp Leu Thr Glu Ala Arg Lys Glu Thr Val
        275                 280                 285

Met Gly Gln Pro Thr Pro Lys Thr Pro Arg Gln Leu Arg Glu Phe Leu
290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Thr Leu Phe Asn Trp
                325                 330                 335

Gly Pro Asp Gln Gln Lys Ala Tyr Gln Glu Ile Lys Gln Ala Leu Leu
            340                 345                 350

Thr Ala Pro Ala Leu Gly Leu Pro Asp Leu Thr Lys Pro Phe Glu Leu
        355                 360                 365

Phe Val Asp Glu Lys Gln Gly Tyr Ala Lys Gly Val Leu Thr Gln Lys
370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
            420                 425                 430

Val Ile Leu Ala Pro Tyr Ala Val Glu Ala Leu Val Lys Gln Pro Pro
        435                 440                 445

Asp Arg Trp Leu Ser Asn Ala Arg Met Thr His Tyr Gln Ala Leu Leu
450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
            500                 505                 510

Pro Leu Pro Asp Ala Asp His Thr Trp Tyr Thr Asp Gly Ser Ser Leu
        515                 520                 525

Leu Gln Glu Gly Gln Arg Lys Ala Gly Ala Ala Val Thr Thr Glu Thr
530                 535                 540

Glu Val Ile Trp Ala Lys Ala Leu Pro Ala Gly Thr Ser Ala Gln Arg
545                 550                 555                 560

Ala Glu Leu Ile Ala Leu Thr Gln Ala Leu Lys Met Ala Glu Gly Lys
                565                 570                 575

Lys Leu Asn Val Tyr Thr Asp Ser Arg Tyr Ala Phe Ala Thr Ala His
            580                 585                 590

Ile His Gly Glu Ile Tyr Arg Arg Gly Leu Leu Thr Ser Glu Gly
        595                 600                 605

Lys Glu Ile Lys Asn Lys Asp Glu Ile Leu Ala Leu Leu Lys Ala Leu
610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
                645                 650                 655

Arg Lys Ala Ala Ile Thr Glu Thr Pro Asp Thr Ser Thr Leu Leu Ile
            660                 665                 670
```

<210> SEQ ID NO 9
<211> LENGTH: 672
<212> TYPE: PRT
<213> ORGANISM: Moloney Murine Leukemia Virus
<220> FEATURE:
<221> NAME/KEY: MUTAGEN
<222> LOCATION: (454)
<223> OTHER INFORMATION: mutant reverse transcriptase having phenylalanine residue instead of asparagine residue at 454 position of SEQ. ID. No: 1

<400> SEQUENCE: 9

```
Met Leu Asn Ile Glu Asp Glu His Arg Leu His Glu Thr Ser Lys Glu
  1               5                  10                  15

Pro Asp Val Ser Leu Gly Ser Thr Trp Leu Ser Asp Phe Pro Gln Ala
             20                  25                  30

Trp Ala Glu Thr Gly Gly Met Gly Leu Ala Val Arg Gln Ala Pro Leu
         35                  40                  45

Ile Ile Pro Leu Lys Ala Thr Ser Thr Pro Val Ser Ile Lys Gln Tyr
     50                  55                  60

Pro Met Ser Gln Glu Ala Arg Leu Gly Ile Lys Pro His Ile Gln Arg
 65                  70                  75                  80

Leu Leu Asp Gln Gly Ile Leu Val Pro Cys Gln Ser Pro Trp Asn Thr
                 85                  90                  95

Pro Leu Leu Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Gly Leu Pro Pro Ser His Gln
    130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190

Lys Asn Ser Pro Thr Leu Phe Asp Glu Ala Leu His Arg Asp Leu Ala
        195                 200                 205

Asp Phe Arg Ile Gln His Pro Asp Leu Ile Leu Leu Gln Tyr Val Asp
    210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Val Lys Tyr Leu Gly Tyr Leu
            260                 265                 270

Leu Lys Glu Gly Gln Arg Trp Leu Thr Glu Ala Arg Lys Glu Thr Val
        275                 280                 285

Met Gly Gln Pro Thr Pro Lys Thr Pro Arg Gln Leu Arg Glu Phe Leu
    290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Thr Leu Phe Asn Trp
                325                 330                 335

Gly Pro Asp Gln Gln Lys Ala Tyr Gln Glu Ile Lys Gln Ala Leu Leu
            340                 345                 350
```

```
Thr Ala Pro Ala Leu Gly Leu Pro Asp Leu Thr Lys Pro Phe Glu Leu
        355                 360                 365

Phe Val Asp Glu Lys Gln Gly Tyr Ala Lys Gly Val Leu Thr Gln Lys
        370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                    405                 410                 415

Ala Val Leu Thr Lys Asp Ala Gly Lys Leu Thr Met Gly Gln Pro Leu
            420                 425                 430

Val Ile Leu Ala Pro His Ala Val Glu Ala Leu Val Lys Gln Pro Pro
            435                 440                 445

Asp Arg Trp Leu Ser Phe Ala Arg Met Thr His Tyr Gln Ala Leu Leu
        450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                    485                 490                 495

Asp Ile Leu Ala Glu Ala His Gly Thr Arg Pro Asp Leu Thr Asp Gln
            500                 505                 510

Pro Leu Pro Asp Ala Asp His Thr Trp Tyr Thr Asp Gly Ser Ser Leu
        515                 520                 525

Leu Gln Glu Gly Gln Arg Lys Ala Gly Ala Ala Val Thr Thr Glu Thr
        530                 535                 540

Glu Val Ile Trp Ala Lys Ala Leu Pro Ala Gly Thr Ser Ala Gln Arg
545                 550                 555                 560

Ala Glu Leu Ile Ala Leu Thr Gln Ala Leu Lys Met Ala Glu Gly Lys
                    565                 570                 575

Lys Leu Asn Val Tyr Thr Asp Ser Arg Tyr Ala Phe Ala Thr Ala His
            580                 585                 590

Ile His Gly Glu Ile Tyr Arg Arg Gly Leu Leu Thr Ser Glu Gly
        595                 600                 605

Lys Glu Ile Lys Asn Lys Asp Glu Ile Leu Ala Leu Leu Lys Ala Leu
        610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
                    645                 650                 655

Arg Lys Ala Ala Ile Thr Glu Thr Pro Asp Thr Ser Thr Leu Leu Ile
            660                 665                 670
```

<210> SEQ ID NO 10
<211> LENGTH: 2016
<212> TYPE: DNA
<213> ORGANISM: Moloney Murine Leukemia Virus
<220> FEATURE:
<221> NAME/KEY: mat_peptide
<222> LOCATION: (1)..(2016)
<223> OTHER INFORMATION: nucleotide sequence coding for the amino acid
      sequence of SEQ. ID. No: 1

<400> SEQUENCE: 10 atgctaaaata tagaagatga gcatcggcta catgagacct caaaagagcc agatgtttct      60
ctagggtcca catggctgtc tgattttcct caggcctggg cggaaaccgg ggcatggga      120 ctggcagttc gccaagctcc tctgatcata cctctgaaag caacctctac ccccgtgtcc      180

```
ataaaacaat accccatgtc acaagaagcc agactgggga tcaagcccca catacagaga    240
ctgttggacc agggaatact ggtaccctgc cagtccccct ggaacacgcc cctgctaccc    300
gttaagaaac cagggactaa tgattatagg cctgtccagg atctgagaga agtcaacaag    360
cgggtggaag acatccaccc caccgtgccc aacccttaca acctcttgag cgggctccca    420
ccgtcccacc agtggtacac tgtgcttgat ttaaaggatg ccttttttctg cctgagactc    480 caccccacca gtcagcctct cttcgccttt gagtggagag atccagagat gggaatctca    540
ggacaattga cctggaccag actcccacag ggtttcaaaa acagtcccac cctgtttgat    600
gaggcactgc acagagacct agcagacttc cggatccagc cccagacctt gatcctgcta    660
cagtacgtgg atgacttact gctggccgcc acttctgagc tagactgcca acaaggtact    720
cgggccctgt tacaaaccct agggaacctc gggtatcggg cctcggccaa gaaagcccaa    780
atttgccaga acaggtcaa gtatctgggg tatcttctaa aagagggtca gagatggctg    840
actgaggcca gaaaagagac tgtgatgggg cagcctactc cgaagacccc tcgacaacta    900
agggagttcc tagggacggc aggcttctgt cgcctctgga tccctgggtt tgcagaaatg    960 gcagcccct tgtaccctct caccaaaacg gggactctgt ttaattgggg cccagaccaa    1020
caaaaggcct atcaagaaat caagcaagct cttctaactg ccccagccct ggggttgcca    1080
gatttgacta gcccctttga actctttgtc gacgagaagc agggctacgc caaaggtgtc    1140
ctaacgcaaa aactgggacc ttggcgtcgg ccggtggcct acctgtccaa aaagctagac    1200
ccagtagcag ctgggtggcc cccttgccta cggatggtag cagccattgc cgtactgaca    1260
aaggatgcag gcaagctaac catgggacag ccactagtca ttctggcccc ccatgcagta    1320
gaggcactag tcaaacaacc ccccgaccgc tggctttcca acgccggat gactcactat    1380 caggccttgc ttttggacac ggaccgggtc cagttcggac cggtggtagc cctgaacccg    1440
gctacgctgc tcccactgcc tgaggaaggg ctgcaacaca actgccttga tatcctggcc    1500
gaagcccacg gaacccgacc cgacctaacg gaccagccgc tcccagacgc cgaccacacc    1560
tggtacacgg atggaagcag tctcttacaa gagggacagc gtaaggcggg agctgcggtg    1620
accaccgaga ccgaggtaat ctgggctaaa gccctgccag ccgggacatc cgctcagcgg    1680
gctgaactga tagcactcac ccaggcccta aagatggcag aaggtaagaa gctaaatgtt    1740
tatactgata gccgttatgc ttttgctact gcccatatcc atggagaaat atacagaagg    1800
cgtgggttgc tcacatcaga aggcaaagag atcaaaaata agacgagat cttggcccta    1860 ctaaaagccc tctttctgcc caaaagactt agcataatcc attgtccagg acatcaaaag    1920
ggacacagcg ccgaggctag aggcaaccgg atggctgacc aagcggcccg aaaggcagcc    1980
atcacagaga ctccagacac ctctaccctc tcata                               2016
```

<210> SEQ ID NO 11
<211> LENGTH: 2016
<212> TYPE: DNA
<213> ORGANISM: Moloney Murine Leukemia Virus
<220> FEATURE:
<221> NAME/KEY: mat_peptide
<222> LOCATION: (1)..(2016)
<223> OTHER INFORMATION: nucleotide sequence coding for the amino acid
      sequence of SEQ. ID. No: 2
<220> FEATURE:
<221> NAME/KEY: mutation
<222> LOCATION: (187)..(189)
<223> OTHER INFORMATION: substitution of ctt instead of caa at 187-189
      positions of SEQ. ID. No: 10

<400> SEQUENCE: 11

```
atgctaaata tagaagatga gcatcggcta catgagacct caaaagagcc agatgtttct      60
ctagggtcca catggctgtc tgattttcct caggcctggg cggaaaccgg gggcatggga     120
ctggcagttc gccaagctcc tctgatcata cctctgaaag caacctctac ccccgtgtcc     180
ataaaacttt accccatgtc acaagaagcc agactgggga tcaagcccca catacagaga     240
ctgttggacc agggaatact ggtaccctgc cagtcccect ggaacacgcc cctgctaccc     300
gttaagaaac cagggactaa tgattatagg cctgtccagg atctgagaga agtcaacaag     360
cgggtggaag acatccaccc caccgtgccc aacccttaca acctcttgag cgggctccca     420
ccgtcccacc agtggtacac tgtgcttgat ttaaaggatg ccttttttctg cctgagactc     480
caccccacca gtcagcctct cttcgccttt gagtggagag atccagagat gggaatctca     540
ggacaattga cctggaccag actcccacag ggtttcaaaa acagtcccac cctgtttgat     600
gaggcactgc acagagacct agcagacttc cggatccagc cccagactt gatcctgcta     660
cagtacgtgg atgacttact gctggccgcc acttctgagc tagactgcca acaaggtact     720
cgggccctgt tacaaaccct agggaaacctc gggtatcggg cctcggccaa gaaagcccaa     780
atttgccaga acaggtcaa gtatctgggg tatcttctaa aagagggtca gagatggctg     840
actgaggcca gaaaagagac tgtgatgggg cagcctactc cgaagacccc tcgacaacta     900
agggagttcc tagggacggc aggcttctgt cgcctctgga tccctgggtt tgcagaaatg     960
gcagccccct tgtaccctct caccaaaacg gggactctgt ttaattgggg cccagaccaa    1020
caaaaggcct atcaagaaat caagcaagct cttctaactg ccccagccct ggggttgcca    1080
gatttgacta agccctttga actctttgtc gacgagaagc agggctacgc caaaggtgtc    1140
ctaacgcaaa aactgggacc ttggcgtcgg ccggtggcct acctgtccaa aaagctagac    1200
ccagtagcag ctgggtggcc cccttgccta cggatggtag cagccattgc cgtactgaca    1260
aaggatgcag gcaagctaac catgggacag ccactagtca ttctggcccc ccatgcagta    1320
gaggcactag tcaaacaacc ccccgaccgc tggctttcca acgcccggat gactcactat    1380
caggccttgc ttttggacac ggaccgggtc cagttcggac cggtggtagc cctgaacccg    1440
gctacgctgc tcccactgcc tgaggaaggg ctgcaacaca actgccttga tatcctggcc    1500
gaagcccacg gaacccgacc cgacctaacg gaccagccgc tcccagacgc cgaccacacc    1560
tggtacacgg atggaagcag tctcttacaa gagggacagc gtaaggcggg agctgcggtg    1620
accaccgaga ccgaggtaat ctgggctaaa gccctgccag ccgggacatc cgctcagcgg    1680
gctgaactga tagcactcac ccaggcccta aagatggcag aaggtaagaa gctaaatgtt    1740
tatactgata gccgttatgc ttttgctact gcccatatcc atggagaaat atacagaagg    1800
cgtgggttgc tcacatcaga aggcaaagag atcaaaaata agacgagat cttggcccta    1860
ctaaaagccc tctttctgcc caaaagactt agcataatcc attgtccagg acatcaaaag    1920
ggacacagcg ccgaggctag aggcaaccgg atggctgacc aagcggcccg aaaggcagcc    1980
atcacagaga ctccagacac ctctaccctc ctcata                              2016
```

<210> SEQ ID NO 12
<211> LENGTH: 2016
<212> TYPE: DNA
<213> ORGANISM: Moloney Murine Leukemia Virus
<220> FEATURE:
<221> NAME/KEY: mat_peptide
<222> LOCATION: (1)..(2016)
<223> OTHER INFORMATION: nucleotide sequence coding for the amino acid sequence of SEQ. ID. No: 3
<220> FEATURE:
<221> NAME/KEY: mutation
<222> LOCATION: (790)..(792)
<223> OTHER INFORMATION: substitution of ctt instead of aaa at 790-792
      positions of SEQ. ID. No: 10

<400> SEQUENCE: 12

```
atgctaaata tagaagatga gcatcggcta catgagacct caaaagagcc agatgtttct      60
ctagggtcca catggctgtc tgattttcct caggcctggg cggaaaccgg gggcatggga     120
ctggcagttc gccaagctcc tctgatcata cctctgaaag caacctctac ccccgtgtcc     180
ataaaacaat accccatgtc acaagaagcc agactgggga tcaagcccca catacagaga     240
ctgttggacc agggaatact ggtaccctgc cagtcccct ggaacacgcc cctgctaccc      300
gttaagaaac cagggactaa tgattatagg cctgtccagg atctgagaga agtcaacaag     360
cgggtggaag acatccaccc caccgtgccc aaccttaca acctcttgag cgggctccca     420
ccgtcccacc agtggtacac tgtgcttgat ttaaaggatg ccttttctg cctgagactc      480
caccccacca gtcagcctct cttcgccttt gagtggagag atccagagat gggaatctca     540
ggacaattga cctggaccag actcccacag ggtttcaaaa acagtcccac cctgtttgat     600
gaggcactgc acagagacct agcagacttc cggatccagc ccagactt gatcctgcta       660
cagtacgtgg atgacttact gctggccgcc acttctgagc tagactgcca acaaggtact     720
cgggccctgt tacaaaccct agggaacctc gggtatcggg cctcggccaa gaaagcccaa     780
atttgccagc ttcaggtcaa gtatctgggg tatcttctaa agagggtca gagatggctg      840
actgaggcca gaaaagagac tgtgatgggg cagcctactc cgaagacccc tcgacaacta    900
agggagttcc tagggacggc aggcttctgt cgcctctgga tccctgggtt tgcagaaatg    960
gcagccccct tgtaccctct caccaaaacg gggactctgt ttaattgggg cccagaccaa   1020
caaaaggcct atcaagaaat caagcaagct cttctaactg ccccagccct gggggttgcca  1080
gatttgacta agcccttttga actctttgtc gacgagaagc agggctacgc caaaggtgtc  1140
ctaacgcaaa aactgggacc ttggcgtcgg ccggtggcct acctgtccaa aaagctagac   1200
ccagtagcag ctgggtggcc cccttgccta cggatggtag cagccattgc cgtactgaca  1260
aaggatgcag gcaagctaac catgggacag ccactagtca ttctggcccc ccatgcagta   1320
gaggcactag tcaaacaacc ccccgaccgc tggctttcca acgcccggat gactcactat   1380
caggccttgc ttttggacac ggaccgggtc cagttcggac cggtggtagc cctgaacccg   1440
gctacgctgc tcccactgcc tgaggaaggg ctgcaacaca actgccttga tatcctggcc   1500
gaagcccacg gaacccgacc cgacctaacg gaccagccgc tcccagacgc cgaccacacc   1560
tggtacacg atgaagcag tctcttacaa gagggacagt gtaaggcggg agctgcggtg     1620
accaccgaga ccgaggtaat ctgggctaaa gccctgccag ccgggacatc cgctcagcgg   1680
gctgaactga tagcactcac ccaggcccta agatggcag aagtaagaa gctaaatgtt      1740
tatactgata gccgttatgc ttttgctact gcccatatcc atggagaaat atacagaagg   1800
cgtgggttgc tcacatcaga aggcaaagag atcaaaaata agacgagat cttggcccta    1860
ctaaaagccc tctttctgcc caaaagactt agcataatcc attgtccagg acatcaaaag   1920
ggacacagcg ccgaggctag aggcaaccgg atggctgacc aagcggcccg aaaggcagcc   1980
atcacagaga ctccagacac ctctacccct ctcata                             2016
```

<210> SEQ ID NO 13

<211> LENGTH: 2016
<212> TYPE: DNA
<213> ORGANISM: Moloney Murine Leukemia Virus
<220> FEATURE:
<221> NAME/KEY: mat_peptide
<222> LOCATION: (1)..(2016)
<223> OTHER INFORMATION: nucleotide sequence coding for the amino acid
      sequence of SEQ. ID. No: 4
<220> FEATURE:
<221> NAME/KEY: mutation
<222> LOCATION: (883)..(885)
<223> OTHER INFORMATION: substitution of caa instead of aag at 883-885
      positions of SEQ. ID. No: 10

<400> SEQUENCE: 13

```
atgctaaata tagaagatga gcatcggcta catgagacct caaaagagcc agatgtttct      60
ctagggtcca catggctgtc tgattttcct caggcctggg cggaaaccgg gggcatggga    120
ctggcagttc gccaagctcc tctgatcata cctctgaaag caacctctac ccccgtgtcc    180
ataaaacaat accccatgtc acaagaagcc agactgggga tcaagcccca catacagaga    240
ctgttggacc agggaatact ggtaccctgc cagtccccct ggaacacgcc cctgctaccc    300
gttaagaaac cagggactaa tgattatagg cctgtccagg atctgagaga agtcaacaag    360
cgggtggaag acatccaccc caccgtgccc aaccctttaca acctcttgag cgggctccca    420
ccgtcccacc agtggtacac tgtgcttgat ttaaaggatg ccttttttctg cctgagactc    480
caccccacca gtcagcctct cttcgccttt gagtggagag atccagagat gggaatctca    540
ggacaattga cctggaccag actcccacag ggtttcaaaa acagtccac cctgtttgat    600
gaggcactgc acagagacct agcagacttc cggatccagc acccagactt gatcctgcta    660
cagtacgtgg atgacttact gctggccgcc acttctgagc tagactgcca acaaggtact    720
cgggccctgt acaaaccct agggaacctc gggtatcggg cctcggccaa gaaagcccaa    780
atttgccaga acaggtcaa gtatctgggg tatcttctaa agagggtca gagatggctg    840
actgaggcca gaaagagac tgtgatgggg cagcctactc cgcaaacccc tcgacaacta    900
agggagttcc tagggacggc aggcttctgt cgcctctgga tccctgggtt tgcagaaatg    960
gcagccccct tgtaccctct caccaaaacg gggactctgt taattgggg cccagaccaa   1020
caaaaggcct atcaagaaat caagcaagct cttctaactg ccccagccct ggggttgcca   1080
gatttgacta gcccctttga actctttgtc gacgagaagc agggctacgc caaaggtgtc   1140
ctaacgcaaa aactgggacc ttggcgtcgg ccggtggcct acctgtccaa aaagctagac   1200
ccagtagcag ctgggtggcc cccttgccta cggatggtag cagccattgc cgtactgaca   1260
aaggatgcag gcaagctaac catgggacag ccactagtca ttctggcccc ccatgcagta   1320
gaggcactag tcaaacaacc ccccgaccgc tggcttttcca acgccggat gactcactat   1380
caggccttgc ttttggacac ggaccgggtc cagttcggac cggtggtagc cctgaacccg   1440
gctacgctgc tcccactgcc tgaggaaggg ctgcaacaca actgccttga tatcctggcc   1500
gaagcccacg gaacccgacc cgacctaacg gaccagccgc tcccagacgc cgaccacacc   1560
tggtacacgg atggaagcag tctcttacaa gagggacagc gtaaggcggg agctgcggtg   1620
accaccgaga ccgaggtaat ctgggctaaa gccctgccag ccgggacatc cgctcagcgg   1680
gctgaactga tagcactcac ccaggcccta aagatggcag aaggtaagaa gctaaatgtt   1740
tatactgata gccgttatgc ttttgctact gcccatatcc atggagaaat atacagaagg   1800
cgtgggttgc tcacatcaga aggcaaagag atcaaaaata agacgagat cttgccccta   1860
ctaaaagccc tctttctgcc caaaagactt agcataatcc attgtccagg acatcaaaag   1920
```

```
ggacacagcg ccgaggctag aggcaaccgg atggctgacc aagcggcccg aaaggcagcc    1980
atcacagaga ctccagacac ctctaccctc ctcata                               2016
```

<210> SEQ ID NO 14
<211> LENGTH: 2016
<212> TYPE: DNA
<213> ORGANISM: Moloney Murine Leukemia Virus
<220> FEATURE:
<221> NAME/KEY: mat_peptide
<222> LOCATION: (1)..(2016)
<223> OTHER INFORMATION: nucleotide sequence coding for the amino acid
      sequence of SEQ. ID. No: 5
<220> FEATURE:
<221> NAME/KEY: mutation
<222> LOCATION: (916)..(918)
<223> OTHER INFORMATION: substitution of ctt instead of acg at 916-918
      positions of SEQ. ID. No: 10

<400> SEQUENCE: 14

```
atgctaaata tagaagatga gcatcggcta catgagacct caaaagagcc agatgtttct     60
ctagggtcca catggctgtc tgattttcct caggcctggg cggaaaccgg gggcatggga    120
ctggcagttc gccaagctcc tctgatcata cctctgaaag caacctctac ccccgtgtcc    180
ataaaacaat accccatgtc acaagaagcc agactgggga tcaagcccca catacagaga    240
ctgttggacc agggaatact ggtaccctgc cagtccccct ggaacacgcc cctgctaccc    300
gttaagaaac cagggactaa tgattatagg cctgtccagg atctgagaga agtcaacaag    360
cgggtggaag acatccaccc caccgtgccc aacccttaca acctcttgag cgggctccca    420
ccgtcccacc agtggtacac tgtgcttgat ttaaaggatg cctttttctg cctgagactc    480
caccccacca gtcagcctct cttcgccttt gagtggagag atccagagat gggaatctca    540
ggacaattga cctggaccag actcccacag ggtttcaaaa acagtccac cctgtttgat    600 gaggcactgc acagagacct agcagacttc cggatccagc cccagactt gatcctgcta    660 cagtacgtgg atgacttact gctggccgcc acttctgagc tagactgcca acaaggtact    720
cgggccctgt tacaaaccct agggaacctc gggtatcggg cctcggccaa gaaagcccaa    780
atttgccaga aacaggtcaa gtatctgggg tatcttctaa aagagggtca gagatggctg    840
actgaggcca aaaagagac tgtgatgggg cagcctactc cgaagacccc tcgacaacta    900
agggagttcc tagggcttgc aggcttctgt cgcctctgga tccctgggtt tgcagaaatg    960 gcagcccct tgtaccctct caccaaaacg gggactctgt ttaattgggg cccagaccaa    1020
caaaaggcct atcaagaaat caagcaagct cttctaactg ccccagccct ggggttgcca    1080
gatttgacta gcccctttga actctttgtc gacgagaagc agggctacgc caaaggtgtc    1140
ctaacgcaaa aactgggacc ttggcgtcgg ccggtggcct acctgtccaa aaagctagac    1200
ccagtagcag ctgggtggcc cccttgccta cggatggtag cagccattgc cgtactgaca    1260
aaggatgcag gcaagctaac catgggacag ccactagtca ttctggcccc catgcagta    1320 gaggcactag tcaaacaacc ccccgaccgc tggctttcca acgcccggat gactcactat    1380
caggccttgc ttttggacac ggaccgggtc cagttcggac cggtggtagc cctgaacccg    1440
gctacgctgt ccccactgcc tgaggaaggg ctgcaacaca actgccttga tatcctggcc    1500
gaagcccacg gaacccgacc cgacctaacg gaccagccgc tcccagacgc cgaccacacc    1560
tggtacacgg atggaagcag tctccttaca gagggacagc gtaaggcggg agctgcggtg    1620
accaccgaga ccgaggtaat ctgggctaaa gccctgccag ccgggacatc cgctcagcgg    1680
```

| gctgaactga tagcactcac ccaggcccta aagatggcag aaggtaagaa gctaaatgtt | 1740 |
| tatactgata gccgttatgc ttttgctact gcccatatcc atggagaaat atacagaagg | 1800 |
| cgtgggttgc tcacatcaga aggcaaagag atcaaaaata agacgagat cttggccta | 1860 |
| ctaaaagccc tctttctgcc caaaagactt agcataatcc attgtccagg acatcaaaag | 1920 |
| ggacacagcg ccgaggctag aggcaaccgg atggctgacc aagcggcccg aaaggcagcc | 1980 |
| atcacagaga ctccagacac ctctaccctc ctcata | 2016 |

<210> SEQ ID NO 15
<211> LENGTH: 2016
<212> TYPE: DNA
<213> ORGANISM: Moloney Murine Leukemia Virus
<220> FEATURE:
<221> NAME/KEY: mat_peptide
<222> LOCATION: (1)..(2016)
<223> OTHER INFORMATION: nucleotide sequence coding for the amino acid
      sequence of SEQ. ID. No: 6
<220> FEATURE:
<221> NAME/KEY: mutation
<222> LOCATION: (1036)..(1038)
<223> OTHER INFORMATION: substitution of atg instead of gaa at 1036-1038
      positions of SEQ. ID. No: 10

<400> SEQUENCE: 15

| atgctaaata tagaagatga gcatcggcta catgagacct caaaagagcc agatgtttct | 60 |
| ctagggtcca catggctgtc tgattttcct caggcctggg cggaaaccgg ggcatggga | 120 |
| ctggcagttc gccaagctcc tctgatcata cctctgaaag caacctctac ccccgtgtcc | 180 |
| ataaacaat accccatgtc acaagaagcc agactgggga tcaagcccca catacagaga | 240 |
| ctgttggacc agggaatact ggtaccctgc cagtccccct ggaacacgcc cctgctaccc | 300 |
| gttaagaaac cagggactaa tgattatagg cctgtccagg atctgagaga agtcaacaag | 360 |
| cgggtggaag acatccaccc caccgtgccc aaccettaca acctcttgag cgggctccca | 420 |
| ccgtcccacc agtggtacac tgtgcttgat ttaaaggatg cctttttctg cctgagactc | 480 |
| caccccacca gtcagcctct cttcgccttt gagtggagag atccagagat gggaatctca | 540 |
| ggacaattga cctggaccag actcccacag ggtttcaaaa acagtcccac cctgtttgat | 600 |
| gaggcactgc acagagacct agcagacttc cggatccagc acccagactt gatcctgcta | 660 |
| cagtacgtgg atgacttact gctggccgcc acttctgagc tagactgcca acaaggtact | 720 |
| cgggccctgt acaaaccct agggaacctc gggtatcggg cctcggccaa gaaagcccaa | 780 |
| atttgccaga acaggtcaa gtatctgggg tatcttctaa agagggtca gagatggctg | 840 |
| actgaggcca gaaaagagac tgtgatgggg cagcctactc gaagaccccc tcgacaacta | 900 |
| agggagttcc tagggacggc aggcttctgt cgcctctgga tccctgggtt tgcagaaatg | 960 |
| gcagccccct tgtaccctct caccaaaacg gggactctgt taattgggg cccagaccaa | 1020 |
| caaaaggcct atcaaatgat caagcaagct cttctaactg ccccagccct ggggttgcca | 1080 |
| gatttgacta gccctttga actctttgtc gacgagaagc agggctacgc caaggtgtc | 1140 |
| ctaacgcaaa aactgggacc ttggcgtcgg ccggtggcct acctgtccaa aaagctagac | 1200 |
| ccagtagcag ctgggtggcc cccttgccta cggatggtag cagccattgc cgtactgaca | 1260 |
| aaggatgcag gcaagctaac catgggacag ccactagtca ttctggcccc ccatgcagta | 1320 |
| gaggcactag tcaaacaacc ccccgaccgc tggcttttcca acgcccggat gactcactat | 1380 |
| caggccttgc ttttgacac ggaccgggtc cagttcggac cggtggtagc cctgaacccg | 1440 |
| gctacgctgc tcccactgcc tgaggaaggg ctgcaacaca actgccttga tatcctggcc | 1500 |

```
gaagcccacg gaacccgacc cgacctaacg gaccagccgc tcccagacgc cgaccacacc   1560
tggtacacgg atggaagcag tctcttacaa gagggacagg gtaaggcggg agctgcggtg   1620
accaccgaga ccgaggtaat ctgggctaaa gccctgccag ccgggacatc cgctcagcgg   1680
gctgaactga tagcactcac ccaggcccta aagatggcga aagtaagaa gctaaatgtt    1740 tatactgata gccgttatgc ttttgctact gcccatatcc atggagaaat atacagaagg   1800
cgtgggttgc tcacatcaga aggcaaagag atcaaaaata aagacgagat cttgccccta   1860
ctaaaagccc tctttctgcc caaaagactt agcataatcc attgtccagg acatcaaaag   1920
ggacacagcg ccgaggctag aggcaaccgg atggctgacc aagcggcccg aaaggcagcc   1980
atcacagaga ctccagacac ctctaccctc ctcata                             2016
```

<210> SEQ ID NO 16
<211> LENGTH: 2016
<212> TYPE: DNA
<213> ORGANISM: Moloney Murine Leukemia Virus
<220> FEATURE:
<221> NAME/KEY: mat_peptide
<222> LOCATION: (1)..(2016)
<223> OTHER INFORMATION: nucleotide sequence coding for the amino acid
      sequence of SEQ. ID. No: 7
<220> FEATURE:
<221> NAME/KEY: mutation
<222> LOCATION: (1222)..(1224)
<223> OTHER INFORMATION: substitution of gaa instead of cct at 1222-1224
      positions of SEQ. ID. No: 10

<400> SEQUENCE: 16

```
atgctaaata tagaagatga gcatcggcta catgagacct caaaagagcc agatgtttct     60
ctagggtcca catggctgtc tgattttcct caggcctggg cggaaaccgg gggcatggga    120
ctggcagttc gccaagctcc tctgatcata cctctgaaag caacctctac ccccgtgtcc    180
ataaaacaat accccatgtc acaagaagcc agactgggga tcaagcccca catacagaga    240
ctgttggacc agggaatact ggtaccctgc cagtccccct ggaacacgcc cctgctaccc    300
gttaagaaac cagggactaa tgattatagg cctgtccagg atctgagaga agtcaacaag    360
cgggtggaag acatccaccc caccgtgccc aaccccttaca acctcttgag cgggctccca    420
ccgtcccacc agtggtacac tgtgcttgat ttaaaggatg cctttttctg cctgagactc    480
caccccacca gtcagcctct cttcgccttt gagtggagag atccagagat gggaatctca    540
ggacaattga cctggaccag actcccacag ggtttcaaaa acagtcccac cctgtttgat    600
gaggcactgc acagagacct agcagacttc cggatccagc acccagactt gatcctgcta    660
cagtacgtgg atgacttact gctggccgcc acttctgagc tagactgcca acaaggtact    720
cgggccctgt tacaaaccct agggaacctc gggtatcggg cctcggccaa gaaagcccaa    780
atttgccaga aacaggtcaa gtatctgggg tatcttctaa agagggtca gagatggctg    840 actgaggcca gaaagagac tgtgatgggg cagcctactc cgaagacccc tcgacaacta    900
agggagttcc tagggacggc aggcttctgt cgcctctgga tccctgggtt tgcagaaatg    960 gcagcccccct tgtaccctct caccaaaacg gggactctgt ttaattgggg cccagaccaa   1020
caaaaggcct atcaagaaat caagcaagct cttctaactg ccccagccct ggggttgcca   1080
gatttgacta agccctttga actctttgtc gacgagaagc agggctacgc caaaggtgtc   1140
ctaacgcaaa aactgggacc ttggcgtcgg ccggtggcct acctgtccaa aaagctagac   1200
ccagtagcag ctgggtggcc cgaatgccta cggatggtag cagccattgc cgtactgaca   1260
```

| | |
|---|---|
| aaggatgcag gcaagctaac catgggacag ccactagtca ttctggcccc ccatgcagta | 1320 |
| gaggcactag tcaaacaacc ccccgaccgc tggctttcca acgcccggat gactcactat | 1380 |
| caggccttgc ttttggacac ggaccgggtc cagttcggac cggtggtagc cctgaacccg | 1440 |
| gctacgctgc tcccactgcc tgaggaaggg ctgcaacaca actgccttga tatcctggcc | 1500 |
| gaagcccacg gaacccgacc cgacctaacg gaccagccgc tcccagacgc cgaccacacc | 1560 |
| tggtacacgg atggaagcag tctcttacaa gagggacagg gtaaggcggg agctgcggtg | 1620 |
| accaccgaga ccgaggtaat ctgggctaaa gccctgccag ccgggacatc cgctcagcgg | 1680 |
| gctgaactga tagcactcac ccaggcccta aagatggcag aaggtaagaa gctaaatgtt | 1740 |
| tatactgata gccgttatgc ttttgctact gcccatatcc atggagaaat atacagaagg | 1800 |
| cgtgggttgc tcacatcaga aggcaaagag atcaaaaata aagacgagat cttggcccta | 1860 |
| ctaaaagccc tctttctgcc caaaagactt agcataatcc attgtccagg acatcaaaag | 1920 |
| ggacacagcg ccgaggctag aggcaaccgg atggctgacc aagcggcccg aaaggcagcc | 1980 |
| atcacagaga ctccagacac ctctaccctc ctcata | 2016 |

```
<210> SEQ ID NO 17
<211> LENGTH: 2016
<212> TYPE: DNA
<213> ORGANISM: Moloney Murine Leukemia Virus
<220> FEATURE:
<221> NAME/KEY: mat_peptide
<222> LOCATION: (1)..(2016)
<223> OTHER INFORMATION: nucleotide sequence coding for the amino acid
      sequence of SEQ. ID. No: 8
<220> FEATURE:
<221> NAME/KEY: mutation
<222> LOCATION: (1312)..(1314)
<223> OTHER INFORMATION: substitution of tac instead of cat at 1312-1314
      positions of SEQ. ID. No: 10

<400> SEQUENCE: 17
```

| | |
|---|---|
| atgctaaata tagaagatga gcatcggcta catgagacct caaaagagcc agatgtttct | 60 |
| ctagggtcca catggctgtc tgattttcct caggcctggg cggaaaccgg gggcatggga | 120 |
| ctggcagttc gccaagctcc tctgatcata cctctgaaag caacctctac ccccgtgtcc | 180 |
| ataaaacaat accccatgtc acaagaagcc agactgggga tcaagcccca catacagaga | 240 |
| ctgttggacc agggaatact ggtaccctgc cagtcccccct ggaacacgcc cctgctaccc | 300 |
| gttaagaaac cagggactaa tgattatagg cctgtccagg atctgagaga agtcaacaag | 360 |
| cgggtggaag acatccaccc caccgtgccc aaccttaca acctcttgag cgggctccca | 420 |
| ccgtcccacc agtggtacac tgtgcttgat ttaaaggatg cctttttctg cctgagactc | 480 |
| cacccccacca gtcagcctct cttcgccttt gagtggagag atccagagat gggaatctca | 540 |
| ggacaattga cctggaccag actcccacag ggtttcaaaa acagtccac cctgtttgat | 600 |
| gaggcactgc acagacctag cagacttcc ggatccagc acccagactt gatcctgcta | 660 |
| cagtacgtgg atgacttact gctggccgcc acttctgagc tagactgcca acaaggtact | 720 |
| cgggccctgt acaaaccct agggaacctc gggtatcggg cctcggccaa gaaagcccaa | 780 |
| atttgccaga acaggtcaa gtatctgggg tatcttctaa aagagggtca gagatggctg | 840 |
| actgaggcca gaaaagagac tgtgatgggg cagcctactc gaagaccc tcgacaacta | 900 |
| agggagttcc tagggacggc aggcttctgt cgcctctgga tccctgggtt tgcagaaatg | 960 |
| gcagccccct tgtaccctct caccaaaacg gggactctgt ttaattgggg cccagaccaa | 1020 |
| caaaaggcct atcaagaaat caagcaagct cttctaactg ccccagccct ggggttgcca | 1080 |

-continued

| | |
|---|---|
| gatttgacta agcccttcga actctttgtc gacgagaagc agggctacgc caaaggtgtc | 1140 |
| ctaacgcaaa aactgggacc ttggcgtcgg ccggtggcct acctgtccaa aaagctagac | 1200 |
| ccagtagcag ctgggtggcc cccttgccta cggatggtag cagccattgc cgtactgaca | 1260 |
| aaggatgcag gcaagctaac catgggacag ccactagtca ttctggcccc ctacgcagta | 1320 |
| gaggcactag tcaaacaacc ccccgaccgc tggctttcca acgcccggat gactcactat | 1380 |
| caggccttgc ttttggacac ggaccgggtc cagttcggac cggtggtagc cctgaacccg | 1440 |
| gctacgctgc tcccactgcc tgaggaaggg ctgcaacaca actgccttga tatcctggcc | 1500 |
| gaagcccacg gaacccgacc cgacctaacg gaccagccgc tcccagacgc cgaccacacc | 1560 |
| tggtacacgg atggaagcag tctcttacaa gagggacagc gtaaggcggg agctgcggtg | 1620 |
| accaccgaga ccgaggtaat ctgggctaaa gccctgccag ccgggacatc cgctcagcgg | 1680 |
| gctgaactga tagcactcac ccaggcccta aagatggcag aaggtaagaa gctaaatgtt | 1740 |
| tatactgata gccgttatgc ttttgctact gcccatatcc atggagaaat atacagaagg | 1800 |
| cgtgggttgc tcacatcaga aggcaaagag atcaaaaata agacgagat cttggcccta | 1860 |
| ctaaaagccc tctttctgcc caaaagactt agcataatcc attgtccagg acatcaaaag | 1920 |
| ggacacagcg ccgaggctag aggcaaccgg atggctgacc aagcggcccg aaaggcagcc | 1980 |
| atcacagaga ctccagacac ctctaccctc ctcata | 2016 |

<210> SEQ ID NO 18
<211> LENGTH: 2016
<212> TYPE: DNA
<213> ORGANISM: Moloney Murine Leukemia Virus
<220> FEATURE:
<221> NAME/KEY: mat_peptide
<222> LOCATION: (1)..(2016)
<223> OTHER INFORMATION: nucleotide sequence coding for the amino acid
      sequence of SEQ. ID. No: 9
<220> FEATURE:
<221> NAME/KEY: mutation
<222> LOCATION: (1360)..(1362)
<223> OTHER INFORMATION: substitution of ttc instead of aac at 1360-1362
      positions of SEQ. ID. No: 10

<400> SEQUENCE: 18

| | |
|---|---|
| atgctaaaata tagaagatga gcatcggcta catgagacct caaaagagcc agatgtttct | 60 |
| ctagggtcca catggctgtc tgattttcct caggcctggg cggaaaccgg ggcatggga | 120 |
| ctggcagttc gccaagctcc tctgatcata cctctgaaag caacctctac ccccgtgtcc | 180 |
| ataaaacaat accccatgtc acaagaagcc agactgggga tcaagcccca catacagaga | 240 |
| ctgttggacc agggaatact ggtaccctgc cagtcccccct ggaacacgcc cctgctaccc | 300 |
| gttaagaaac cagggactaa tgattatagg cctgtccagg atctgagaga agtcaacaag | 360 |
| cgggtggaag acatccaccc caccgtgccc aaccttaca acctcttgag cgggctccca | 420 |
| ccgtcccacc agtggtacac tgtgcttgat ttaaaggatg cctttttctg cctgagactc | 480 |
| caccccacca gtcagcctct cttcgccttt gagtggagag atccagagat gggaatctca | 540 |
| ggacaattga cctggaccag actcccacag gtttcaaaa acagtccac cctgtttgat | 600 |
| gaggcactgc acagagacct agcagacttc cggatccagc acccagactt gatcctgcta | 660 |
| cagtacgtgg atgacttact gctggccgcc acttctgagc tagactgcca acaaggtact | 720 |
| cgggcccctgt tacaaacccct agggaacctc gggtatcggg cctcggccaa gaaagcccaa | 780 |
| atttgccaga aacaggtcaa gtatctgggg tatcttctaa aagagggtca gagatggctg | 840 |

```
actgaggcca gaaaagagac tgtgatgggg cagcctactc cgaagacccc tcgacaacta    900
agggagttcc tagggacggc aggcttctgt cgcctctgga tccctgggtt tgcagaaatg    960 gcagcccect tgtaccctct caccaaaacg gggactctgt ttaattgggg cccagaccaa   1020
caaaaggcct atcaagaaat caagcaagct cttctaactg ccccagccct ggggttgcca   1080
gatttgacta agcccttga actctttgtc gacgagaagc agggctacgc caaaggtgtc    1140
ctaacgcaaa aactgggacc ttggcgtcgg ccggtggcct acctgtccaa aaagctagac   1200
ccagtagcag ctgggtggcc cccttgccta cggatggtag cagccattgc cgtactgaca   1260
aaggatgcag gcaagctaac catgggacag ccactagtca ttctggcccc ccatgcagta   1320
gaggcactag tcaaacaacc ccccgaccgc tggctttcct tcgcccggat gactcactat   1380
caggccttgc ttttggacac ggaccgggtc cagttcggac cggtggtagc cctgaacccg   1440
gctacgctgc tcccactgcc tgaggaaggg ctgaacaca actgccttga tatcctggcc    1500
gaagcccacg gaacccgacc cgacctaacg gaccagccgc tcccagacgc cgaccacacc   1560
tggtacacgg atggaagcag tctcttacaa gagggacagc gtaaggcggg agctgcggtg   1620
accaccgaga ccgaggtaat ctgggctaaa gccctgccag ccgggacatc cgctcagcgg   1680
gctgaactga tagcactcac ccaggcccta aagatgcag aaggtaagaa gctaaatgtt    1740
tatactgata gccgttatgc ttttgctact gcccatatcc atggagaaat atacagaagg   1800
cgtgggttgc tcacatcaga aggcaaagag atcaaaaata agacgagat cttggcccta    1860 ctaaaagccc tctttctgcc caaaagactt agcataatcc attgtccagg acatcaaaag   1920
ggacacagcg ccgaggctag aggcaaccgg atggctgacc aagcggcccg aaaggcagcc   1980
atcacagaga ctccagacac ctctaccctc tcata                             2016
```

<210> SEQ ID NO 19
<211> LENGTH: 2019
<212> TYPE: DNA
<213> ORGANISM: Artificial Sequence
<220> FEATURE:
<223> OTHER INFORMATION: Optimized Moloney Murine Leukemia Virus reverse
      transcriptase in accordance with codon usage
<220> FEATURE:
<221> NAME/KEY: mat_peptide
<222> LOCATION: (1)..(2016)
<223> OTHER INFORMATION: nucleotide sequence coding for the amino acid
      sequence of SEQ. ID. No: 1

<400> SEQUENCE: 19

```
atgctgaaca tcgaagacga acaccgtctg cacgaaacct ctaaagaacc ggacgtttct     60
ctgggttcta cctggctgtc tgacttcccg caggcttggg ctgaaaccgg tggtatgggt    120
ctggctgttc gtcaggctcc gctgatcatc ccgctgaaag ctacctctac cccggttcct    180
atcaaacagt acccgatgtc tcaggaagct cgtctgggta tcaaaccgca catccagcgt    240
ctgctggacc agggtatcct ggttccgtgc cagtctccgt ggaacacccc gctgctgccg    300
gttaaaaaac cgggtaccaa cgactaccgt ccggttcagg acctgcgtga agttaacaaa    360
cgtgttgaag acatccaccc gaccgttccg aacccgtaca acctgctgtc tggtctgccg    420
ccgtctcacc agtggtacac cgttctggac ctgaaagacg cttttcttctg cctgcgtctg    480 cacccgacct ctcagccgct gttcgctttc gaatggcgtg accggaaat gggtatctct    540 ggtcagctga cctggaccg tctgccgcag ggtttcaaaa actctccgac cctgttcgac    600
gaagctctgc accgtgacct ggctgacttc cgtatccagc accggacct gatcctgctg    660 cagtacgttg acgacctgct gctggctgct acctctgaac tggactgcca gcagggtacc    720
```

-continued

```
cgtgctctgc tgcagaccct gggtaacctg ggttaccgtg cttctgctaa aaaagctcag      780
atctgccaga aacaggttaa atacctgggt tacctgctga agaaggtca gcgttggctg       840 accgaagctc gtaaagaaac cgttatgggt cagccgaccc cgaaaacccc gcgtcagctg      900
cgtgaattcc tgggtaccgc tggtttctgc cgtctgtgga taccgggttt cgctgaaatg      960
gctgctccgc tgtacccgct gaccaaaacc ggtaccctgt tcaactgggg tccggaccag     1020
cagaaagcgt accaggaaat caaacaggct ctgctgaccg ctccggctct gggtctgccg     1080
gacctgacca aaccgttcga actgttcgtt gacgaaaaac agggttacgc taaaggtgtt     1140
ctgacccaga aactgggtcc gtggcgtcgt ccggttgctt acctgtctaa aaaactggac     1200
ccggttgctg ctggttggcc gccgtgcctg cgtatggttg ctgctatcgc tgttctgacc     1260
aaagacgctg gtaaactgac catgggtcag ccgctggtta tcctggctcc gcacgctgtt     1320
gaagctctgg ttaaacagcc gccggaccgt tggctgtcta cgctcgtat gacccactac      1380 caggctctgc tgctggacac cgaccgtgtt cagttcggtc cggttgttgc tctgaacccg     1440
gctaccctgc tgccgctgcc ggaagaaggt ctgcagcaca actgcctgga catcctggct     1500
gaagctcacg gtaccgtcc ggacctgacc gaccagccgc tgccgacgc tgaccacacc      1560 tggtacaccg acggttcttc tctgctgcag gaaggtcagc gtaaagctgg tgctgctgtt     1620
accaccgaaa ccgaagttat ctgggctaaa gctctgccgg ctggtacctc tgctcagcgt     1680
gctgaactga tcgctctgac ccaggctctg aaaatggctg aaggtaaaaa actgaacgtt     1740
tacaccgact ctcgttacgc tttcgctacc gctcacatcc acggtgaaat ctaccgtcgt     1800
cgtggtctgc tgacctctga aggtaaagaa atcaaaaaca aagacgaaat cctggctctg     1860
ctgaaagctc tgttcctgcc gaaacgtctg tctatcatcc actgcccggg tcaccagaaa     1920
ggtcactctg ctgaagctcg tggtaaccgt atggctgacc aggctgctcg taaagctgct     1980
atcaccgaaa ccccggacac ctctacccctg ctgatctaa                            2019
```

<210> SEQ ID NO 20
<211> LENGTH: 19
<212> TYPE: DNA
<213> ORGANISM: Artificial Sequence
<220> FEATURE:
<223> OTHER INFORMATION: R0 oligonucleotide

<400> SEQUENCE: 20
ttcagggata gagggagta                                                    19

<210> SEQ ID NO 21
<211> LENGTH: 36
<212> TYPE: DNA
<213> ORGANISM: Artificial Sequence
<220> FEATURE:
<223> OTHER INFORMATION: F0 oligonucleotide

<400> SEQUENCE: 21
tactccctct atccctgaac atcgaagacg aacacc                                 36

<210> SEQ ID NO 22
<211> LENGTH: 33
<212> TYPE: DNA
<213> ORGANISM: Artificial Sequence
<220> FEATURE:
<223> OTHER INFORMATION: R19 oligonucleotide

<400> SEQUENCE: 22

```
gaggtttcgt gcagacggtg ttcgtcttcg atg                                33
```

<210> SEQ ID NO 23
<211> LENGTH: 34
<212> TYPE: DNA
<213> ORGANISM: Artificial Sequence
<220> FEATURE:
<223> OTHER INFORMATION: F36 oligonucleotide

<400> SEQUENCE: 23

```
gtctgcacga aacctctaaa gaaccggacg tttc                               34
```

<210> SEQ ID NO 24
<211> LENGTH: 34
<212> TYPE: DNA
<213> ORGANISM: Artificial Sequence
<220> FEATURE:
<223> OTHER INFORMATION: R52 oligonucleotide

<400> SEQUENCE: 24

```
ccaggtagaa cccagagaaa cgtccggttc ttta                               34
```

<210> SEQ ID NO 25
<211> LENGTH: 32
<212> TYPE: DNA
<213> ORGANISM: Artificial Sequence
<220> FEATURE:
<223> OTHER INFORMATION: F70 oligonucleotide

<400> SEQUENCE: 25

```
tctgggttct acctggctgt ctgacttccc gc                                 32
```

<210> SEQ ID NO 26
<211> LENGTH: 30
<212> TYPE: DNA
<213> ORGANISM: Artificial Sequence
<220> FEATURE:
<223> OTHER INFORMATION: R86 oligonucleotide

<400> SEQUENCE: 26

```
ttcagcccaa gcctgcggga agtcagacag                                    30
```

<210> SEQ ID NO 27
<211> LENGTH: 29
<212> TYPE: DNA
<213> ORGANISM: Artificial Sequence
<220> FEATURE:
<223> OTHER INFORMATION: F102 oligonucleotide

<400> SEQUENCE: 27

```
aggcttgggc tgaaaccggt ggtatgggt                                     29
```

<210> SEQ ID NO 28
<211> LENGTH: 30
<212> TYPE: DNA
<213> ORGANISM: Artificial Sequence
<220> FEATURE:
<223> OTHER INFORMATION: R116 oligonucleotide

<400> SEQUENCE: 28

```
ctgacgaaca gccagaccca taccaccggt                                    30
```

<210> SEQ ID NO 29
<211> LENGTH: 30
<212> TYPE: DNA
<213> ORGANISM: Artificial Sequence

```
<220> FEATURE:
<223> OTHER INFORMATION: F131 oligonucleotide

<400> SEQUENCE: 29
ctggctgttc gtcaggctcc gctgatcatc                                    30

<210> SEQ ID NO 30
<211> LENGTH: 30
<212> TYPE: DNA
<213> ORGANISM: Artificial Sequence
<220> FEATURE:
<223> OTHER INFORMATION: R146 oligonucleotide

<400> SEQUENCE: 30
ggtagctttc agcgggatga tcagcggagc                                    30

<210> SEQ ID NO 31
<211> LENGTH: 33
<212> TYPE: DNA
<213> ORGANISM: Artificial Sequence
<220> FEATURE:
<223> OTHER INFORMATION: F161 oligonucleotide

<400> SEQUENCE: 31
ccgctgaaag ctacctctac cccggtttct atc                                33

<210> SEQ ID NO 32
<211> LENGTH: 35
<212> TYPE: DNA
<213> ORGANISM: Artificial Sequence
<220> FEATURE:
<223> OTHER INFORMATION: R176 oligonucleotide

<400> SEQUENCE: 32
gacatcgggt actgtttgat agaaaccggg gtaga                              35

<210> SEQ ID NO 33
<211> LENGTH: 33
<212> TYPE: DNA
<213> ORGANISM: Artificial Sequence
<220> FEATURE:
<223> OTHER INFORMATION: F194 oligonucleotide

<400> SEQUENCE: 33
aaacagtacc cgatgtctca ggaagctcgt ctg                                33

<210> SEQ ID NO 34
<211> LENGTH: 32
<212> TYPE: DNA
<213> ORGANISM: Artificial Sequence
<220> FEATURE:
<223> OTHER INFORMATION: R211 oligonucleotide

<400> SEQUENCE: 34
tgtgcggttt gatacccaga cgagcttcct ga                                 32

<210> SEQ ID NO 35
<211> LENGTH: 30
<212> TYPE: DNA
<213> ORGANISM: Artificial Sequence
<220> FEATURE:
<223> OTHER INFORMATION: F227 oligonucleotide

<400> SEQUENCE: 35
ggtatcaaac cgcacatcca gcgtctgctg                                    30
```

<210> SEQ ID NO 36
<211> LENGTH: 30
<212> TYPE: DNA
<213> ORGANISM: Artificial Sequence
<220> FEATURE:
<223> OTHER INFORMATION: R243 oligonucleotide

<400> SEQUENCE: 36
ccaggatacc ctggtccagc agacgctgga                              30

<210> SEQ ID NO 37
<211> LENGTH: 31
<212> TYPE: DNA
<213> ORGANISM: Artificial Sequence
<220> FEATURE:
<223> OTHER INFORMATION: F257 oligonucleotide

<400> SEQUENCE: 37
gaccagggta tcctggttcc gtgccagtct c                            31

<210> SEQ ID NO 38
<211> LENGTH: 29
<212> TYPE: DNA
<213> ORGANISM: Artificial Sequence
<220> FEATURE:
<223> OTHER INFORMATION: R273 oligonucleotide

<400> SEQUENCE: 38
cggggtgttc cacggagact ggcacggaa                               29

<210> SEQ ID NO 39
<211> LENGTH: 29
<212> TYPE: DNA
<213> ORGANISM: Artificial Sequence
<220> FEATURE:
<223> OTHER INFORMATION: F288 oligonucleotide

<400> SEQUENCE: 39
cgtggaacac cccgctgctg ccggttaaa                               29

<210> SEQ ID NO 40
<211> LENGTH: 31
<212> TYPE: DNA
<213> ORGANISM: Artificial Sequence
<220> FEATURE:
<223> OTHER INFORMATION: R302 oligonucleotide

<400> SEQUENCE: 40
cgttggtacc cggttttttta accggcagca g                           31

<210> SEQ ID NO 41
<211> LENGTH: 31
<212> TYPE: DNA
<213> ORGANISM: Artificial Sequence
<220> FEATURE:
<223> OTHER INFORMATION: F317 oligonucleotide

<400> SEQUENCE: 41
aaaccgggta ccaacgacta ccgtccggtt c                            31

<210> SEQ ID NO 42
<211> LENGTH: 30
<212> TYPE: DNA
<213> ORGANISM: Artificial Sequence
<220> FEATURE:
<223> OTHER INFORMATION: R333 oligonucleotide

<400> SEQUENCE: 42
cttcacgcag gtcctgaacc ggacggtagt                                    30

<210> SEQ ID NO 43
<211> LENGTH: 35
<212> TYPE: DNA
<213> ORGANISM: Artificial Sequence
<220> FEATURE:
<223> OTHER INFORMATION: F348 oligonucleotide

<400> SEQUENCE: 43
aggacctgcg tgaagttaac aaacgtgttg aagac                              35

<210> SEQ ID NO 44
<211> LENGTH: 34
<212> TYPE: DNA
<213> ORGANISM: Artificial Sequence
<220> FEATURE:
<223> OTHER INFORMATION: R363 oligonucleotide

<400> SEQUENCE: 44
acggtcgggt ggatgtcttc aacacgtttg ttaa                               34

<210> SEQ ID NO 45
<211> LENGTH: 29
<212> TYPE: DNA
<213> ORGANISM: Artificial Sequence
<220> FEATURE:
<223> OTHER INFORMATION: F383 oligonucleotide

<400> SEQUENCE: 45
atccacccga ccgttccgaa cccgtacaa                                     29

<210> SEQ ID NO 46
<211> LENGTH: 30
<212> TYPE: DNA
<213> ORGANISM: Artificial Sequence
<220> FEATURE:
<223> OTHER INFORMATION: R397 oligonucleotide

<400> SEQUENCE: 46
agaccagaca gcaggttgta cgggttcgga                                    30

<210> SEQ ID NO 47
<211> LENGTH: 27
<212> TYPE: DNA
<213> ORGANISM: Artificial Sequence
<220> FEATURE:
<223> OTHER INFORMATION: F412 oligonucleotide

<400> SEQUENCE: 47
cctgctgtct ggtctgccgc cgtctca                                       27

<210> SEQ ID NO 48
<211> LENGTH: 27
<212> TYPE: DNA
<213> ORGANISM: Artificial Sequence
<220> FEATURE:
<223> OTHER INFORMATION: R427 oligonucleotide

<400> SEQUENCE: 48
acggtgtacc actggtgaga cggcggc                                       27

<210> SEQ ID NO 49

```
<211> LENGTH: 32
<212> TYPE: DNA
<213> ORGANISM: Artificial Sequence
<220> FEATURE:
<223> OTHER INFORMATION: F439 oligonucleotide

<400> SEQUENCE: 49
ccagtggtac accgttctgg acctgaaaga cg                                32

<210> SEQ ID NO 50
<211> LENGTH: 33
<212> TYPE: DNA
<213> ORGANISM: Artificial Sequence
<220> FEATURE:
<223> OTHER INFORMATION: R454 oligonucleotide

<400> SEQUENCE: 50
cgcaggcaga agaaagcgtc tttcaggtcc aga                               33

<210> SEQ ID NO 51
<211> LENGTH: 30
<212> TYPE: DNA
<213> ORGANISM: Artificial Sequence
<220> FEATURE:
<223> OTHER INFORMATION: F471 oligonucleotide

<400> SEQUENCE: 51
ctttcttctg cctgcgtctg cacccgacct                                   30

<210> SEQ ID NO 52
<211> LENGTH: 29
<212> TYPE: DNA
<213> ORGANISM: Artificial Sequence
<220> FEATURE:
<223> OTHER INFORMATION: R487 oligonucleotide

<400> SEQUENCE: 52
cgaacagcgg ctgagaggtc gggtgcaga                                    29

<210> SEQ ID NO 53
<211> LENGTH: 31
<212> TYPE: DNA
<213> ORGANISM: Artificial Sequence
<220> FEATURE:
<223> OTHER INFORMATION: F501 oligonucleotide

<400> SEQUENCE: 53
ctcagccgct gttcgctttc gaatggcgtg a                                 31

<210> SEQ ID NO 54
<211> LENGTH: 33
<212> TYPE: DNA
<213> ORGANISM: Artificial Sequence
<220> FEATURE:
<223> OTHER INFORMATION: R516 oligonucleotide

<400> SEQUENCE: 54
agatacccat ttccgggtca cgccattcga aag                               33

<210> SEQ ID NO 55
<211> LENGTH: 32
<212> TYPE: DNA
<213> ORGANISM: Artificial Sequence
<220> FEATURE:
<223> OTHER INFORMATION: F532 oligonucleotide

<400> SEQUENCE: 55
```
cccggaaatg ggtatctctg gtcagctgac ct                                         32

<210> SEQ ID NO 56
<211> LENGTH: 28
<212> TYPE: DNA
<213> ORGANISM: Artificial Sequence
<220> FEATURE:
<223> OTHER INFORMATION: R549 oligonucleotide

<400> SEQUENCE: 56
ggcagacggg tccaggtcag ctgaccag                                              28

<210> SEQ ID NO 57
<211> LENGTH: 31
<212> TYPE: DNA
<213> ORGANISM: Artificial Sequence
<220> FEATURE:
<223> OTHER INFORMATION: F564 oligonucleotide

<400> SEQUENCE: 57
ggacccgtct gccgcagggt ttcaaaaact c                                          31

<210> SEQ ID NO 58
<211> LENGTH: 32
<212> TYPE: DNA
<213> ORGANISM: Artificial Sequence
<220> FEATURE:
<223> OTHER INFORMATION: R577 oligonucleotide

<400> SEQUENCE: 58
cgaacagggt cggagagttt ttgaaaccct gc                                         32

<210> SEQ ID NO 59
<211> LENGTH: 29
<212> TYPE: DNA
<213> ORGANISM: Artificial Sequence
<220> FEATURE:
<223> OTHER INFORMATION: F595 oligonucleotide

<400> SEQUENCE: 59
tccgaccctg ttcgacgaag ctctgcacc                                             29

<210> SEQ ID NO 60
<211> LENGTH: 30
<212> TYPE: DNA
<213> ORGANISM: Artificial Sequence
<220> FEATURE:
<223> OTHER INFORMATION: R609 oligonucleotide

<400> SEQUENCE: 60
agtcagccag gtcacggtgc agagcttcgt                                            30

<210> SEQ ID NO 61
<211> LENGTH: 30
<212> TYPE: DNA
<213> ORGANISM: Artificial Sequence
<220> FEATURE:
<223> OTHER INFORMATION: F624 oligonucleotide

<400> SEQUENCE: 61
gtgacctggc tgacttccgt atccagcacc                                            30

<210> SEQ ID NO 62
<211> LENGTH: 30
<212> TYPE: DNA

```
<213> ORGANISM: Artificial Sequence
<220> FEATURE:
<223> OTHER INFORMATION: R639 oligonucleotide

<400> SEQUENCE: 62
gcaggatcag gtccgggtgc tggatacgga                                    30

<210> SEQ ID NO 63
<211> LENGTH: 31
<212> TYPE: DNA
<213> ORGANISM: Artificial Sequence
<220> FEATURE:
<223> OTHER INFORMATION: F654 oligonucleotide

<400> SEQUENCE: 63
cggacctgat cctgctgcag tacgttgacg a                                  31

<210> SEQ ID NO 64
<211> LENGTH: 29
<212> TYPE: DNA
<213> ORGANISM: Artificial Sequence
<220> FEATURE:
<223> OTHER INFORMATION: R669 oligonucleotide

<400> SEQUENCE: 64
agccagcagc aggtcgtcaa cgtactgca                                     29

<210> SEQ ID NO 65
<211> LENGTH: 30
<212> TYPE: DNA
<213> ORGANISM: Artificial Sequence
<220> FEATURE:
<223> OTHER INFORMATION: F685 oligonucleotide

<400> SEQUENCE: 65
cctgctgctg gctgctacct ctgaactgga                                    30

<210> SEQ ID NO 66
<211> LENGTH: 30
<212> TYPE: DNA
<213> ORGANISM: Artificial Sequence
<220> FEATURE:
<223> OTHER INFORMATION: R698 oligonucleotide

<400> SEQUENCE: 66
accctgctgg cagtccagtt cagaggtagc                                    30

<210> SEQ ID NO 67
<211> LENGTH: 26
<212> TYPE: DNA
<213> ORGANISM: Artificial Sequence
<220> FEATURE:
<223> OTHER INFORMATION: F715 oligonucleotide

<400> SEQUENCE: 67
ctgccagcag ggtacccgtg ctctgc                                        26

<210> SEQ ID NO 68
<211> LENGTH: 28
<212> TYPE: DNA
<213> ORGANISM: Artificial Sequence
<220> FEATURE:
<223> OTHER INFORMATION: R728 oligonucleotide

<400> SEQUENCE: 68
tacccagggt ctgcagcaga gcacgggt                                      28
```

<210> SEQ ID NO 69
<211> LENGTH: 30
<212> TYPE: DNA
<213> ORGANISM: Artificial Sequence
<220> FEATURE:
<223> OTHER INFORMATION: F741 oligonucleotide

<400> SEQUENCE: 69
tgcagaccct gggtaacctg ggttaccgtg                                30

<210> SEQ ID NO 70
<211> LENGTH: 35
<212> TYPE: DNA
<213> ORGANISM: Artificial Sequence
<220> FEATURE:
<223> OTHER INFORMATION: R756 oligonucleotide

<400> SEQUENCE: 70
ctgagctttt ttagcagaag cacggtaacc caggt                          35

<210> SEQ ID NO 71
<211> LENGTH: 37
<212> TYPE: DNA
<213> ORGANISM: Artificial Sequence
<220> FEATURE:
<223> OTHER INFORMATION: F771 oligonucleotide

<400> SEQUENCE: 71
cttctgctaa aaagctcag atctgccaga aacaggt                         37

<210> SEQ ID NO 72
<211> LENGTH: 37
<212> TYPE: DNA
<213> ORGANISM: Artificial Sequence
<220> FEATURE:
<223> OTHER INFORMATION: R791 oligonucleotide

<400> SEQUENCE: 72
gcaggtaacc caggtattta acctgtttct ggcagat                        37

<210> SEQ ID NO 73
<211> LENGTH: 37
<212> TYPE: DNA
<213> ORGANISM: Artificial Sequence
<220> FEATURE:
<223> OTHER INFORMATION: F808 oligonucleotide

<400> SEQUENCE: 73
taaatacctg ggttacctgc tgaaagaagg tcagcgt                        37

<210> SEQ ID NO 74
<211> LENGTH: 31
<212> TYPE: DNA
<213> ORGANISM: Artificial Sequence
<220> FEATURE:
<223> OTHER INFORMATION: R828 oligonucleotide

<400> SEQUENCE: 74
gcttcggtca gccaacgctg accttctttc a                              31

<210> SEQ ID NO 75
<211> LENGTH: 34
<212> TYPE: DNA
<213> ORGANISM: Artificial Sequence
<220> FEATURE:

<223> OTHER INFORMATION: F845 oligonucleotide

<400> SEQUENCE: 75
tggctgaccg aagctcgtaa agaaaccgtt atgg                          34

<210> SEQ ID NO 76
<211> LENGTH: 33
<212> TYPE: DNA
<213> ORGANISM: Artificial Sequence
<220> FEATURE:
<223> OTHER INFORMATION: R859 oligonucleotide

<400> SEQUENCE: 76
ggggtcggct gacccataac ggtttcttta cga                           33

<210> SEQ ID NO 77
<211> LENGTH: 27
<212> TYPE: DNA
<213> ORGANISM: Artificial Sequence
<220> FEATURE:
<223> OTHER INFORMATION: F879 oligonucleotide

<400> SEQUENCE: 77
gtcagccgac cccgaaaacc ccgcgtc                                  27

<210> SEQ ID NO 78
<211> LENGTH: 29
<212> TYPE: DNA
<213> ORGANISM: Artificial Sequence
<220> FEATURE:
<223> OTHER INFORMATION: R892 oligonucleotide

<400> SEQUENCE: 78
ggaattcacg cagctgacgc ggggttttc                                29

<210> SEQ ID NO 79
<211> LENGTH: 29
<212> TYPE: DNA
<213> ORGANISM: Artificial Sequence
<220> FEATURE:
<223> OTHER INFORMATION: F906 oligonucleotide

<400> SEQUENCE: 79
agctgcgtga attcctgggt accgctggt                                29

<210> SEQ ID NO 80
<211> LENGTH: 29
<212> TYPE: DNA
<213> ORGANISM: Artificial Sequence
<220> FEATURE:
<223> OTHER INFORMATION: R921 oligonucleotide

<400> SEQUENCE: 80
ccacagacgg cagaaaccag cggtaccca                                29

<210> SEQ ID NO 81
<211> LENGTH: 30
<212> TYPE: DNA
<213> ORGANISM: Artificial Sequence
<220> FEATURE:
<223> OTHER INFORMATION: F935 oligonucleotide

<400> SEQUENCE: 81
ttctgccgtc tgtggatacc gggtttcgct                               30

```
<210> SEQ ID NO 82
<211> LENGTH: 30
<212> TYPE: DNA
<213> ORGANISM: Artificial Sequence
<220> FEATURE:
<223> OTHER INFORMATION: R950 oligonucleotide

<400> SEQUENCE: 82
cggagcagcc atttcagcga aacccggtat                                    30

<210> SEQ ID NO 83
<211> LENGTH: 30
<212> TYPE: DNA
<213> ORGANISM: Artificial Sequence
<220> FEATURE:
<223> OTHER INFORMATION: F965 oligonucleotide

<400> SEQUENCE: 83
gaaatggctg ctccgctgta cccgctgacc                                    30

<210> SEQ ID NO 84
<211> LENGTH: 31
<212> TYPE: DNA
<213> ORGANISM: Artificial Sequence
<220> FEATURE:
<223> OTHER INFORMATION: R980 oligonucleotide

<400> SEQUENCE: 84
acagggtacc ggttttggtc agcgggtaca g                                  31

<210> SEQ ID NO 85
<211> LENGTH: 30
<212> TYPE: DNA
<213> ORGANISM: Artificial Sequence
<220> FEATURE:
<223> OTHER INFORMATION: F995 oligonucleotide

<400> SEQUENCE: 85
aaaaccggta ccctgttcaa ctggggtccg                                    30

<210> SEQ ID NO 86
<211> LENGTH: 29
<212> TYPE: DNA
<213> ORGANISM: Artificial Sequence
<220> FEATURE:
<223> OTHER INFORMATION: R1011 oligonucleotide

<400> SEQUENCE: 86
cgctttctgc tggtccggac cccagttga                                     29

<210> SEQ ID NO 87
<211> LENGTH: 34
<212> TYPE: DNA
<213> ORGANISM: Artificial Sequence
<220> FEATURE:
<223> OTHER INFORMATION: F1025 oligonucleotide

<400> SEQUENCE: 87
gaccagcaga aagcgtacca ggaaatcaaa cagg                               34

<210> SEQ ID NO 88
<211> LENGTH: 33
<212> TYPE: DNA
<213> ORGANISM: Artificial Sequence
<220> FEATURE:
<223> OTHER INFORMATION: R1040 oligonucleotide
```

<400> SEQUENCE: 88
agcggtcagc agagcctgtt tgatttcctg gta                                33

<210> SEQ ID NO 89
<211> LENGTH: 27
<212> TYPE: DNA
<213> ORGANISM: Artificial Sequence
<220> FEATURE:
<223> OTHER INFORMATION: F1059 oligonucleotide

<400> SEQUENCE: 89
ctctgctgac cgctccggct ctgggtc                                       27

<210> SEQ ID NO 90
<211> LENGTH: 27
<212> TYPE: DNA
<213> ORGANISM: Artificial Sequence
<220> FEATURE:
<223> OTHER INFORMATION: R1073 oligonucleotide

<400> SEQUENCE: 90
ggtcaggtcc ggcagaccca gagccgg                                       27

<210> SEQ ID NO 91
<211> LENGTH: 31
<212> TYPE: DNA
<213> ORGANISM: Artificial Sequence
<220> FEATURE:
<223> OTHER INFORMATION: F1086 oligonucleotide

<400> SEQUENCE: 91
tgccggacct gaccaaaccg ttcgaactgt t                                  31

<210> SEQ ID NO 92
<211> LENGTH: 34
<212> TYPE: DNA
<213> ORGANISM: Artificial Sequence
<220> FEATURE:
<223> OTHER INFORMATION: R1100 oligonucleotide

<400> SEQUENCE: 92
cctgtttttc gtcaacgaac agttcgaacg gttt                               34

<210> SEQ ID NO 93
<211> LENGTH: 36
<212> TYPE: DNA
<213> ORGANISM: Artificial Sequence
<220> FEATURE:
<223> OTHER INFORMATION: F1117 oligonucleotide

<400> SEQUENCE: 93
cgttgacgaa aacagggtt acgctaaagg tgttct                              36

<210> SEQ ID NO 94
<211> LENGTH: 35
<212> TYPE: DNA
<213> ORGANISM: Artificial Sequence
<220> FEATURE:
<223> OTHER INFORMATION: R1134 oligonucleotide

<400> SEQUENCE: 94
acccagtttc tgggtcagaa cacctttagc gtaac                              35

<210> SEQ ID NO 95
<211> LENGTH: 28

<210> SEQ ID NO 96
<211> LENGTH: 27
<212> TYPE: DNA
<213> ORGANISM: Artificial Sequence
<220> FEATURE:
<223> OTHER INFORMATION: F1153 oligonucleotide

<400> SEQUENCE: 95
gacccagaaa ctgggtccgt ggcgtcgt                                    28

<210> SEQ ID NO 96
<211> LENGTH: 27
<212> TYPE: DNA
<213> ORGANISM: Artificial Sequence
<220> FEATURE:
<223> OTHER INFORMATION: R1169 oligonucleotide

<400> SEQUENCE: 96
caggtaagca accggacgac gccacgg                                     27

<210> SEQ ID NO 97
<211> LENGTH: 33
<212> TYPE: DNA
<213> ORGANISM: Artificial Sequence
<220> FEATURE:
<223> OTHER INFORMATION: F1181 oligonucleotide

<400> SEQUENCE: 97
ccggttgctt acctgtctaa aaaactggac ccg                              33

<210> SEQ ID NO 98
<211> LENGTH: 33
<212> TYPE: DNA
<213> ORGANISM: Artificial Sequence
<220> FEATURE:
<223> OTHER INFORMATION: R1196 oligonucleotide

<400> SEQUENCE: 98
ccaaccagca gcaaccgggt ccagttttt aga                               33

<210> SEQ ID NO 99
<211> LENGTH: 27
<212> TYPE: DNA
<213> ORGANISM: Artificial Sequence
<220> FEATURE:
<223> OTHER INFORMATION: F1214 oligonucleotide

<400> SEQUENCE: 99
gttgctgctg gttggccgcc gtgcctg                                     27

<210> SEQ ID NO 100
<211> LENGTH: 29
<212> TYPE: DNA
<213> ORGANISM: Artificial Sequence
<220> FEATURE:
<223> OTHER INFORMATION: R1229 oligonucleotide

<400> SEQUENCE: 100
atagcagcaa ccatacgcag gcacggcgg                                   29

<210> SEQ ID NO 101
<211> LENGTH: 33
<212> TYPE: DNA
<213> ORGANISM: Artificial Sequence
<220> FEATURE:
<223> OTHER INFORMATION: F1241 oligonucleotide

<400> SEQUENCE: 101

```
cgtatggttg ctgctatcgc tgttctgacc aaa                                    33

<210> SEQ ID NO 102
<211> LENGTH: 33
<212> TYPE: DNA
<213> ORGANISM: Artificial Sequence
<220> FEATURE:
<223> OTHER INFORMATION: R1258 oligonucleotide

<400> SEQUENCE: 102
gtcagtttac cagcgtcttt ggtcagaaca gcg                                    33

<210> SEQ ID NO 103
<211> LENGTH: 31
<212> TYPE: DNA
<213> ORGANISM: Artificial Sequence
<220> FEATURE:
<223> OTHER INFORMATION: F1274 oligonucleotide

<400> SEQUENCE: 103
gacgctggta aactgaccat gggtcagccg c                                      31

<210> SEQ ID NO 104
<211> LENGTH: 30
<212> TYPE: DNA
<213> ORGANISM: Artificial Sequence
<220> FEATURE:
<223> OTHER INFORMATION: R1291 oligonucleotide

<400> SEQUENCE: 104
ggagccagga taaccagcgg ctgacccatg                                        30

<210> SEQ ID NO 105
<211> LENGTH: 31
<212> TYPE: DNA
<213> ORGANISM: Artificial Sequence
<220> FEATURE:
<223> OTHER INFORMATION: F1305 oligonucleotide

<400> SEQUENCE: 105
tggttatcct ggctccgcac gctgttgaag c                                      31

<210> SEQ ID NO 106
<211> LENGTH: 32
<212> TYPE: DNA
<213> ORGANISM: Artificial Sequence
<220> FEATURE:
<223> OTHER INFORMATION: R1321 oligonucleotide

<400> SEQUENCE: 106
gcggctgttt aaccagagct tcaacagcgt gc                                     32

<210> SEQ ID NO 107
<211> LENGTH: 30
<212> TYPE: DNA
<213> ORGANISM: Artificial Sequence
<220> FEATURE:
<223> OTHER INFORMATION: F1336 oligonucleotide

<400> SEQUENCE: 107
tctggttaaa cagccgccgg accgttggct                                        30

<210> SEQ ID NO 108
<211> LENGTH: 31
<212> TYPE: DNA
<213> ORGANISM: Artificial Sequence
```

```
<220> FEATURE:
<223> OTHER INFORMATION: R1353 oligonucleotide

<400> SEQUENCE: 108
gtcatacgag cgttagacag ccaacggtcc g                              31

<210> SEQ ID NO 109
<211> LENGTH: 34
<212> TYPE: DNA
<213> ORGANISM: Artificial Sequence
<220> FEATURE:
<223> OTHER INFORMATION: F1366 oligonucleotide

<400> SEQUENCE: 109
gtctaacgct cgtatgaccc actaccaggc tctg                           34

<210> SEQ ID NO 110
<211> LENGTH: 30
<212> TYPE: DNA
<213> ORGANISM: Artificial Sequence
<220> FEATURE:
<223> OTHER INFORMATION: R1384 oligonucleotide

<400> SEQUENCE: 110
tcggtgtcca gcagcagagc ctggtagtgg                                30

<210> SEQ ID NO 111
<211> LENGTH: 29
<212> TYPE: DNA
<213> ORGANISM: Artificial Sequence
<220> FEATURE:
<223> OTHER INFORMATION: F1400 oligonucleotide

<400> SEQUENCE: 111
ctgctggaca ccgaccgtgt tcagttcgg                                 29

<210> SEQ ID NO 112
<211> LENGTH: 30
<212> TYPE: DNA
<213> ORGANISM: Artificial Sequence
<220> FEATURE:
<223> OTHER INFORMATION: R1414 oligonucleotide

<400> SEQUENCE: 112
agagcaacaa ccggaccgaa ctgaacacgg                                30

<210> SEQ ID NO 113
<211> LENGTH: 29
<212> TYPE: DNA
<213> ORGANISM: Artificial Sequence
<220> FEATURE:
<223> OTHER INFORMATION: F1429 oligonucleotide

<400> SEQUENCE: 113
tccggttgtt gctctgaacc cggctaccc                                 29

<210> SEQ ID NO 114
<211> LENGTH: 26
<212> TYPE: DNA
<213> ORGANISM: Artificial Sequence
<220> FEATURE:
<223> OTHER INFORMATION: R1444 oligonucleotide

<400> SEQUENCE: 114
gcagcggcag cagggtagcc gggttc                                    26
```

<210> SEQ ID NO 115
<211> LENGTH: 28
<212> TYPE: DNA
<213> ORGANISM: Artificial Sequence
<220> FEATURE:
<223> OTHER INFORMATION: F1458 oligonucleotide

<400> SEQUENCE: 115
tgctgccgct gccggaagaa ggtctgca                                28

<210> SEQ ID NO 116
<211> LENGTH: 30
<212> TYPE: DNA
<213> ORGANISM: Artificial Sequence
<220> FEATURE:
<223> OTHER INFORMATION: R1470 oligonucleotide

<400> SEQUENCE: 116
ccaggcagtt gtgctgcaga ccttcttccg                              30

<210> SEQ ID NO 117
<211> LENGTH: 30
<212> TYPE: DNA
<213> ORGANISM: Artificial Sequence
<220> FEATURE:
<223> OTHER INFORMATION: F1486 oligonucleotide

<400> SEQUENCE: 117
gcacaactgc ctggacatcc tggctgaagc                              30

<210> SEQ ID NO 118
<211> LENGTH: 30
<212> TYPE: DNA
<213> ORGANISM: Artificial Sequence
<220> FEATURE:
<223> OTHER INFORMATION: R1500 oligonucleotide

<400> SEQUENCE: 118
gacgggtacc gtgagcttca gccaggatgt                              30

<210> SEQ ID NO 119
<211> LENGTH: 28
<212> TYPE: DNA
<213> ORGANISM: Artificial Sequence
<220> FEATURE:
<223> OTHER INFORMATION: F1516 oligonucleotide

<400> SEQUENCE: 119
tcacggtacc cgtccggacc tgaccgac                                28

<210> SEQ ID NO 120
<211> LENGTH: 26
<212> TYPE: DNA
<213> ORGANISM: Artificial Sequence
<220> FEATURE:
<223> OTHER INFORMATION: R1530 oligonucleotide

<400> SEQUENCE: 120
cggcagcggc tggtcggtca ggtccg                                  26

<210> SEQ ID NO 121
<211> LENGTH: 27
<212> TYPE: DNA
<213> ORGANISM: Artificial Sequence
<220> FEATURE:
<223> OTHER INFORMATION: F1544 oligonucleotide

<400> SEQUENCE: 121
cagccgctgc cggacgctga ccacacc                                           27

<210> SEQ ID NO 122
<211> LENGTH: 29
<212> TYPE: DNA
<213> ORGANISM: Artificial Sequence
<220> FEATURE:
<223> OTHER INFORMATION: R1556 oligonucleotide

<400> SEQUENCE: 122
ccgtcggtgt accaggtgtg gtcagcgtc                                         29

<210> SEQ ID NO 123
<211> LENGTH: 31
<212> TYPE: DNA
<213> ORGANISM: Artificial Sequence
<220> FEATURE:
<223> OTHER INFORMATION: F1571 oligonucleotide

<400> SEQUENCE: 123
tggtacaccg acggttcttc tctgctgcag g                                      31

<210> SEQ ID NO 124
<211> LENGTH: 33
<212> TYPE: DNA
<213> ORGANISM: Artificial Sequence
<220> FEATURE:
<223> OTHER INFORMATION: R1585 oligonucleotide

<400> SEQUENCE: 124
gctttacgct gaccttcctg cagcagagaa gaa                                    33

<210> SEQ ID NO 125
<211> LENGTH: 33
<212> TYPE: DNA
<213> ORGANISM: Artificial Sequence
<220> FEATURE:
<223> OTHER INFORMATION: F1602 oligonucleotide

<400> SEQUENCE: 125
aaggtcagcg taaagctggt gctgctgtta cca                                    33

<210> SEQ ID NO 126
<211> LENGTH: 36
<212> TYPE: DNA
<213> ORGANISM: Artificial Sequence
<220> FEATURE:
<223> OTHER INFORMATION: R1618 oligonucleotide

<400> SEQUENCE: 126
cagataactt cggtttcggt ggtaacagca gcacca                                 36

<210> SEQ ID NO 127
<211> LENGTH: 35
<212> TYPE: DNA
<213> ORGANISM: Artificial Sequence
<220> FEATURE:
<223> OTHER INFORMATION: F1635 oligonucleotide

<400> SEQUENCE: 127
ccgaaaccga agttatctgg gctaaagctc tgccg                                  35

<210> SEQ ID NO 128

<210> SEQ ID NO 128
<211> LENGTH: 32
<212> TYPE: DNA
<213> ORGANISM: Artificial Sequence
<220> FEATURE:
<223> OTHER INFORMATION: R1654 oligonucleotide

<400> SEQUENCE: 128
gagcagaggt accagccggc agagctttag cc                32

<210> SEQ ID NO 129
<211> LENGTH: 32
<212> TYPE: DNA
<213> ORGANISM: Artificial Sequence
<220> FEATURE:
<223> OTHER INFORMATION: F1670 oligonucleotide

<400> SEQUENCE: 129
gctggtacct ctgctcagcg tgctgaactg at                32

<210> SEQ ID NO 130
<211> LENGTH: 31
<212> TYPE: DNA
<213> ORGANISM: Artificial Sequence
<220> FEATURE:
<223> OTHER INFORMATION: R1686 oligonucleotide

<400> SEQUENCE: 130
gcctgggtca gagcgatcag ttcagcacgc t                 31

<210> SEQ ID NO 131
<211> LENGTH: 35
<212> TYPE: DNA
<213> ORGANISM: Artificial Sequence
<220> FEATURE:
<223> OTHER INFORMATION: F1702 oligonucleotide

<400> SEQUENCE: 131
cgctctgacc caggctctga aaatggctga aggta             35

<210> SEQ ID NO 132
<211> LENGTH: 40
<212> TYPE: DNA
<213> ORGANISM: Artificial Sequence
<220> FEATURE:
<223> OTHER INFORMATION: R1717 oligonucleotide

<400> SEQUENCE: 132
ggtgtaaacg ttcagttttt taccttcagc catttcaga         40

<210> SEQ ID NO 133
<211> LENGTH: 38
<212> TYPE: DNA
<213> ORGANISM: Artificial Sequence
<220> FEATURE:
<223> OTHER INFORMATION: F1737 oligonucleotide

<400> SEQUENCE: 133
aaaaactgaa cgtttacacc gactctcgtt acgctttc          38

<210> SEQ ID NO 134
<211> LENGTH: 34
<212> TYPE: DNA
<213> ORGANISM: Artificial Sequence
<220> FEATURE:
<223> OTHER INFORMATION: R1757 oligonucleotide

<400> SEQUENCE: 134

```
ggatgtgagc ggtagcgaaa gcgtaacgag agtc                          34
```

<210> SEQ ID NO 135
<211> LENGTH: 33
<212> TYPE: DNA
<213> ORGANISM: Artificial Sequence
<220> FEATURE:
<223> OTHER INFORMATION: F1775 oligonucleotide

<400> SEQUENCE: 135

```
gctaccgctc acatccacgg tgaaatctac cgt                           33
```

<210> SEQ ID NO 136
<211> LENGTH: 32
<212> TYPE: DNA
<213> ORGANISM: Artificial Sequence
<220> FEATURE:
<223> OTHER INFORMATION: R1791 oligonucleotide

<400> SEQUENCE: 136

```
cagcagacca cgacgacggt agatttcacc gt                            32
```

<210> SEQ ID NO 137
<211> LENGTH: 35
<212> TYPE: DNA
<213> ORGANISM: Artificial Sequence
<220> FEATURE:
<223> OTHER INFORMATION: F1808 oligonucleotide

<400> SEQUENCE: 137

```
cgtcgtggtc tgctgacctc tgaaggtaaa gaaat                         35
```

<210> SEQ ID NO 138
<211> LENGTH: 40
<212> TYPE: DNA
<213> ORGANISM: Artificial Sequence
<220> FEATURE:
<223> OTHER INFORMATION: R1823 oligonucleotide

<400> SEQUENCE: 138

```
ggatttcgtc tttgtttttg atttctttac cttcagaggt                    40
```

<210> SEQ ID NO 139
<211> LENGTH: 37
<212> TYPE: DNA
<213> ORGANISM: Artificial Sequence
<220> FEATURE:
<223> OTHER INFORMATION: F1843 oligonucleotide

<400> SEQUENCE: 139

```
caaaaacaaa gacgaaatcc tggctctgct gaaagct                       37
```

<210> SEQ ID NO 140
<211> LENGTH: 33
<212> TYPE: DNA
<213> ORGANISM: Artificial Sequence
<220> FEATURE:
<223> OTHER INFORMATION: R1863 oligonucleotide

<400> SEQUENCE: 140

```
gtttcggcag gaacagagct ttcagcagag cca                           33
```

<210> SEQ ID NO 141
<211> LENGTH: 36
<212> TYPE: DNA

```
<213> ORGANISM: Artificial Sequence
<220> FEATURE:
<223> OTHER INFORMATION: F1880 oligonucleotide

<400> SEQUENCE: 141
ctgttcctgc cgaaacgtct gtctatcatc cactgc                              36

<210> SEQ ID NO 142
<211> LENGTH: 34
<212> TYPE: DNA
<213> ORGANISM: Artificial Sequence
<220> FEATURE:
<223> OTHER INFORMATION: R1896 oligonucleotide

<400> SEQUENCE: 142
ttctggtgac ccgggcagtg gatgatagac agac                                34

<210> SEQ ID NO 143
<211> LENGTH: 31
<212> TYPE: DNA
<213> ORGANISM: Artificial Sequence
<220> FEATURE:
<223> OTHER INFORMATION: F1916 oligonucleotide

<400> SEQUENCE: 143
ccgggtcacc agaaaggtca ctctgctgaa g                                   31

<210> SEQ ID NO 144
<211> LENGTH: 34
<212> TYPE: DNA
<213> ORGANISM: Artificial Sequence
<220> FEATURE:
<223> OTHER INFORMATION: R1930 oligonucleotide

<400> SEQUENCE: 144
catacggtta ccacgagctt cagcagagtg acct                                34

<210> SEQ ID NO 145
<211> LENGTH: 31
<212> TYPE: DNA
<213> ORGANISM: Artificial Sequence
<220> FEATURE:
<223> OTHER INFORMATION: F1947 oligonucleotide

<400> SEQUENCE: 145
ctcgtggtaa ccgtatggct gaccaggctg c                                   31

<210> SEQ ID NO 146
<211> LENGTH: 33
<212> TYPE: DNA
<213> ORGANISM: Artificial Sequence
<220> FEATURE:
<223> OTHER INFORMATION: R1964 oligonucleotide

<400> SEQUENCE: 146
ggtgatagca gctttacgag cagcctggtc agc                                 33

<210> SEQ ID NO 147
<211> LENGTH: 34
<212> TYPE: DNA
<213> ORGANISM: Artificial Sequence
<220> FEATURE:
<223> OTHER INFORMATION: F1978 oligonucleotide

<400> SEQUENCE: 147
tcgtaaagct gctatcaccg aaaccccgga cacc                                34
```

<210> SEQ ID NO 148
<211> LENGTH: 33
<212> TYPE: DNA
<213> ORGANISM: Artificial Sequence
<220> FEATURE:
<223> OTHER INFORMATION: R1997 oligonucleotide

<400> SEQUENCE: 148
ttagatcagc agggtagagg tgtccggggt ttc                              33

<210> SEQ ID NO 149
<211> LENGTH: 18
<212> TYPE: DNA
<213> ORGANISM: Artificial Sequence
<220> FEATURE:
<223> OTHER INFORMATION: F2012 oligonucleotide

<400> SEQUENCE: 149
tctaccctgc tgatctaa                                              18

<210> SEQ ID NO 150
<211> LENGTH: 27
<212> TYPE: DNA
<213> ORGANISM: Artificial Sequence
<220> FEATURE:
<223> OTHER INFORMATION: forward primer for the synthesis of K295Q
      mutant

<400> SEQUENCE: 150
gtcagccgac cccgcaaacc ccgcgtc                                    27

<210> SEQ ID NO 151
<211> LENGTH: 29
<212> TYPE: DNA
<213> ORGANISM: Artificial Sequence
<220> FEATURE:
<223> OTHER INFORMATION: reverse primer for the synthesis of K295Q
      mutant

<400> SEQUENCE: 151
ggaattcacg cagctgacgc ggggtttgc                                  29

<210> SEQ ID NO 152
<211> LENGTH: 18
<212> TYPE: DNA
<213> ORGANISM: Artificial Sequence
<220> FEATURE:
<223> OTHER INFORMATION: forward primer for the amplification of
      synthesized gene

<400> SEQUENCE: 152
ctgaacatcg aagacgaa                                              18

<210> SEQ ID NO 153
<211> LENGTH: 18
<212> TYPE: DNA
<213> ORGANISM: Artificial Sequence
<220> FEATURE:
<223> OTHER INFORMATION: reverse primer for the amplification of
      synthesized gene

<400> SEQUENCE: 153
ttagatcagc agggtaga                                              18

<210> SEQ ID NO 154

```
<211> LENGTH: 30
<212> TYPE: DNA
<213> ORGANISM: Artificial Sequence
<220> FEATURE:
<223> OTHER INFORMATION: forward primer for site-directed mutagenesis of
      Q63L

<400> SEQUENCE: 154
caaactttac ccgatgtctc aggaagctcg                                    30

<210> SEQ ID NO 155
<211> LENGTH: 30
<212> TYPE: DNA
<213> ORGANISM: Artificial Sequence
<220> FEATURE:
<223> OTHER INFORMATION: reverse primer for site-directed mutagenesis of
      Q63L

<400> SEQUENCE: 155
atagaaaccg gggtagaggt agctttcagc                                    30

<210> SEQ ID NO 156
<211> LENGTH: 31
<212> TYPE: DNA
<213> ORGANISM: Artificial Sequence
<220> FEATURE:
<223> OTHER INFORMATION: forward primer for site-directed mutagenesis of
      K264L

<400> SEQUENCE: 156
ccagcttcag gttaaatacc tgggttacct g                                  31

<210> SEQ ID NO 157
<211> LENGTH: 30
<212> TYPE: DNA
<213> ORGANISM: Artificial Sequence
<220> FEATURE:
<223> OTHER INFORMATION: reverse primer for site-directed mutagenesis of
      K264L

<400> SEQUENCE: 157
cagatctgag cttttttagc agaagcacgg                                    30

<210> SEQ ID NO 158
<211> LENGTH: 26
<212> TYPE: DNA
<213> ORGANISM: Artificial Sequence
<220> FEATURE:
<223> OTHER INFORMATION: forward primer for site-directed mutagenesis of
      T306L

<400> SEQUENCE: 158
ggtcttgctg gtttctgccg tctgtg                                        26

<210> SEQ ID NO 159
<211> LENGTH: 24
<212> TYPE: DNA
<213> ORGANISM: Artificial Sequence
<220> FEATURE:
<223> OTHER INFORMATION: reverse primer for site-directed mutagenesis of
      T306L

<400> SEQUENCE: 159
caggaattca cgcagctgac gcgg                                          24

<210> SEQ ID NO 160
<211> LENGTH: 28
```

```
<212> TYPE: DNA
<213> ORGANISM: Artificial Sequence
<220> FEATURE:
<223> OTHER INFORMATION: forward primer for site-directed mutagenesis of
      E346M

<400> SEQUENCE: 160
cagatgatca aacaggctct gctgaccg                                        28

<210> SEQ ID NO 161
<211> LENGTH: 24
<212> TYPE: DNA
<213> ORGANISM: Artificial Sequence
<220> FEATURE:
<223> OTHER INFORMATION: reverse primer for site-directed mutagenesis of
      E346M

<400> SEQUENCE: 161
gtacgctttc tgctggtccg gacc                                            24

<210> SEQ ID NO 162
<211> LENGTH: 25
<212> TYPE: DNA
<213> ORGANISM: Artificial Sequence
<220> FEATURE:
<223> OTHER INFORMATION: forward primer for site-directed mutagenesis of
      P408E

<400> SEQUENCE: 162
ccggaatgcc tgcgtatggt tgctg                                           25

<210> SEQ ID NO 163
<211> LENGTH: 22
<212> TYPE: DNA
<213> ORGANISM: Artificial Sequence
<220> FEATURE:
<223> OTHER INFORMATION: reverse primer for site-directed mutagenesis of
      P408E

<400> SEQUENCE: 163
ccaaccagca gcaaccgggt cc                                              22

<210> SEQ ID NO 164
<211> LENGTH: 30
<212> TYPE: DNA
<213> ORGANISM: Artificial Sequence
<220> FEATURE:
<223> OTHER INFORMATION: forward primer for site-directed mutagenesis of
      H438Y

<400> SEQUENCE: 164
cgtacgctgt tgaagctctg gttaaacagc                                      30

<210> SEQ ID NO 165
<211> LENGTH: 25
<212> TYPE: DNA
<213> ORGANISM: Artificial Sequence
<220> FEATURE:
<223> OTHER INFORMATION: reverse primer for site-directed mutagenesis of
      H438Y

<400> SEQUENCE: 165
gagccaggat aaccagcggc tgacc                                           25

<210> SEQ ID NO 166
<211> LENGTH: 30
<212> TYPE: DNA
```

<213> ORGANISM: Artificial Sequence
<220> FEATURE:
<223> OTHER INFORMATION: forward primer for site-directed mutagenesis of
      N454F

<400> SEQUENCE: 166
ctgtctttcg ctcgtatgac ccactaccag                                    30

<210> SEQ ID NO 167
<211> LENGTH: 24
<212> TYPE: DNA
<213> ORGANISM: Artificial Sequence
<220> FEATURE:
<223> OTHER INFORMATION: reverse primer for site-directed mutagenesis of
      N454F

<400> SEQUENCE: 167
ccaacggtcc ggcggctgtt taac                                          24

<210> SEQ ID NO 168
<211> LENGTH: 47
<212> TYPE: DNA
<213> ORGANISM: Artificial Sequence
<220> FEATURE:
<223> OTHER INFORMATION: primer for sense strand of Q63L, K264L, T306L
      and E346M mutant genes

<400> SEQUENCE: 168
gcgcgccata tgctgaacat cgaagacgaa caccgtctgc acgaaac                 47

<210> SEQ ID NO 169
<211> LENGTH: 47
<212> TYPE: DNA
<213> ORGANISM: Artificial Sequence
<220> FEATURE:
<223> OTHER INFORMATION: primer for antisense strand of Q63L, K264L,
      T306L and E346M mutant genes

<400> SEQUENCE: 169
gcgcgcgcgg ccgcttagat cagcagggta gaggtgtccg ggtttc                  47

<210> SEQ ID NO 170
<211> LENGTH: 47
<212> TYPE: DNA
<213> ORGANISM: Artificial Sequence
<220> FEATURE:
<223> OTHER INFORMATION: primer for sense strand of K295Q, P408E, H438Y
      and N454F mutant genes

<400> SEQUENCE: 170
gcgcgccata tgctgaacat cgaagacgaa caccgtctgc acgaaac                 47

<210> SEQ ID NO 171
<211> LENGTH: 44
<212> TYPE: DNA
<213> ORGANISM: Artificial Sequence
<220> FEATURE:
<223> OTHER INFORMATION: primer for antisense strand of K295Q, P408E,
      H438Y and N454F mutant genes

<400> SEQUENCE: 171
gcgcgcgcgg ccgcgatcag cagggtagag gtgtccgggg tttc                    44

<210> SEQ ID NO 172
<211> LENGTH: 20
<212> TYPE: DNA
<213> ORGANISM: Artificial Sequence

```
<220> FEATURE:
<223> OTHER INFORMATION: primer for sense strand of T7 promoter

<400> SEQUENCE: 172
taatacgact cactataggg                                              20

<210> SEQ ID NO 173
<211> LENGTH: 19
<212> TYPE: DNA
<213> ORGANISM: Artificial Sequence
<220> FEATURE:
<223> OTHER INFORMATION: primer for antisense strand of T7 promoter

<400> SEQUENCE: 173
gctagttatt gctcagcgg                                               19

<210> SEQ ID NO 174
<211> LENGTH: 23
<212> TYPE: DNA
<213> ORGANISM: Artificial Sequence
<220> FEATURE:
<223> OTHER INFORMATION: primer for sense strand of GAPDH gene

<400> SEQUENCE: 174
gaaggtgaag gtcggagtca acg                                          23

<210> SEQ ID NO 175
<211> LENGTH: 24
<212> TYPE: DNA
<213> ORGANISM: Artificial Sequence
<220> FEATURE:
<223> OTHER INFORMATION: primer for antisense strand of GAPDH gene

<400> SEQUENCE: 175
agtccttcca cgataccaaa gttg                                         24
```